(12) United States Patent
Benovic et al.

(10) Patent No.: US 6,255,069 B1
(45) Date of Patent: Jul. 3, 2001

(54) COMPOSITIONS AND METHODS FOR MODULATING THE ACTIVITY OF G PROTEIN-COUPLED RECEPTOR KINASES GPK5 AND GRK6

(75) Inventors: Jeffrey L. Benovic, Havertown, PA (US); Jorge Gomez, Wheaton, MD (US); Priya Kunapuli, Upper Darby, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 08/464,954

(22) Filed: Jun. 6, 1995

Related U.S. Application Data

(63) Continuation-in-part of application No. 08/076,084, filed on Jun. 11, 1993, now abandoned.

(51) Int. Cl.[7] .................................................. C12N 15/12
(52) U.S. Cl. .................. 435/69.1; 435/252.3; 435/320.1; 536/23.2
(58) Field of Search ................................ 435/194, 240.2, 435/69.2, 70.1, 69.1, 252.3, 32.1; 536/23.2, 23.5

(56) References Cited

U.S. PATENT DOCUMENTS 5,532,151 * 7/1996 Chantry et al. ...................... 435/194

OTHER PUBLICATIONS

Ambrose, C., James, M., Barnes, G., Lin, C., Bates, G., Altherr, M., Duyao, M., Groot, N., Church, D., Wasmuth, J.J., Lehrach, H., Housman, D., Buckler, A., Gusella, J.F., and MacDonald, M.E., "A novel G protein–coupled receptor kinase gene cloned from 4p16.3", 1992, *Human Mol. Genet.* 1:697–703.

Benovic, J.L., DeBlasi, A., Stone, W.C., Caron, M.G., and Lefkowitz, R.J., "β–Adrenergic Receptor Kinase: Primary Structure Delineates a Multigene Family", 1989, *Science* 246:235–246.

Benovic, J.L., Onorato, J.J., Ariza, J.L., Stone, W.C., Lohse, M., Jenkins, N.A., Gilbert, D.J., Copeland, N.G., Caron, M.G. and Lefkowitz, R.J., "Cloning, Expression, and Chromosomal Localization of β–Adrenergic Receptor Kinase 2", 1991, *J. Biol. Chem.* 266:14939–14946.

Cassill, J.A., Whitney, M., Joazeiro, C.A.P., Becker, A., and Zucker, C.S., "Isolation of Drosophila genes encoding G protein–coupled receptor kinases", 1991, *Proc. Natl. Acad. Sci. USA* 88:11067–11070.

Lorenz, W., Inglese, J., Palczewski, K., Onorato, J.J., Caron, M.G. and Lefkowitz, R.J., "The receptor kinase family: Primary structure of rhodopsin kinase reveals similarities to the β–adrenergic receptor kinase", 1991, *Proc. Natl. Acad. Sci. USA* 88:8715–8719.

Molstad et al (Biochimica Biophysica Acta, 512 , 557), 1978.*

Haribabu et al 1993 (Pans USA, 90,9398).*

* cited by examiner

*Primary Examiner*—John Ulm
(74) *Attorney, Agent, or Firm*—ReedSmith LLP; William J. McNichol, Jr.; Nanda P. B. A. Kumar

(57) ABSTRACT

G protein-coupled receptor kinases (GRK) play an important role in phosphorylating and regulating the activity of G protein-coupled receptors. Complementary DNAs (cDNAs) that encode two novel members of the G protein-coupled receptor kinase (GRK) family are provided in the present invention. These cDNAs encode GRK5 (590 amino acids) and GRK6 (576 amino acids) which represent two new members of the GRK family that have distinct tissue distribution and substrate specificity. The availability of the cDNAs enables the generation of reagents to modulate the activity of endogenous kinases. These include dominant negative mutations and antisense oligonucleotides or stably transfected antisense constructs to block expression of the kinase to generate a cell with a reduced ability to desensitize to various agents. Expression of GRK5 and GRK6 also permits identification of specific inhibitors and activators of these two kinases. Such inhibitors and activators may be used therapeutically to either directly modulate the activity of a given receptor or by augmenting the ability of a given therapeutic agent to stimulate a given receptor.

7 Claims, 14 Drawing Sheets

FIG. 2A

```
                  S  H  K  F  S  E  E  A  K  S  I  C  K  M  L  L  T  K  D  A  K  Q  R  L  G  C  Q  E  E  G  A  A  E  V  K  R  H  P  F  F    448
tcaggaacatgaacttcaagctgcttagaagccggatgttgacctccccttgttcagaccctgttcgttgactgtgctgacatcgagcagttctccactgtgaagg 1682
  R  N  M  F  K  R  L  E  A  G  M  L  D  P  P  F  V  P  D  P  R  A  V  Y  C  K  D  V  L  D  I  E  Q  F  S  T  V  K  G    488
gcgtcaatctgaccacacagacgacgactctactccaagttctccacgggctctgtgtcatccatgcaaaacgagatgcttaaggagctgaacgtgtttg 1802
  V  N  L  D  H  T  D  D  D  F  Y  S  K  F  S  T  G  S  V  S  I  P  W  Q  N  E  M  I  E  T  E  C  F  K  E  L  N  V  F  G    528
gaccaaatgtaccctcccgccagatctgaacagaaaccacctccgaacggcaaagggctgctccagagactcttcaagcggccaagtcagaacaattccaagagttcgccca 1922
  P  N  G  T  L  P  P  D  L  N  R  N  H  P  P  E  P  P  K  K  G  L  L  Q  R  L  F  K  R  P  S  Q  N  N  S  K  S  S  P  S    568
gctccaagaccagttttaaccaccaccataaactcaaaccatgtcagctcagctgaagcagctagttcggctctgcctccaagtccacagtggaccagcccagacccttct 2042
  S  K  T  S  F  N  H  H  I  N  S  N  H  V  S  S  N  S  T  G  S  S                                                             590
ccttagaagtggaagtagtggagcccctgctcgtgggctgcagggagacccggagcccggagccggagaggaggccgtccatccgtcgacgtagaacctcgagtttctcaaagaattt 2162
ccactcagttctgttccgaggcgttggattgttcttggtgaacattgcaatagaaatccaattgcacgtattttaatagcgtcataa 2282
ctagaactgaattttgtctttatgattttgtaaattctctactgtctcagttacattttgtatttaaatgaagtgagactttgagggtgtatat 2402
tttctgtgcagccactgttaagcacatgttgttccaaggcatttagcggggaggggttatcaaaaaaaaaaaatgtgactcaagacttccagagcctcaaatgagaaatgtctttat 2522
taaatgtagaaagtgatccatacttcaaaaaaaa 2557
```

FIG. 2B

```
cgcggcactcgcgcgatcccgcgccggcgccggcgcccggcgccaggcgccgcccacagccggcccacagccgtgctactcaagccggaagtggcg   120
                         M  E  L  E  N  I  V  A  N  T  V  L  K  A  R  E  G  G  G     20 gtggaaatcgcaaaggcaaagcaagaaatggcgcagatgctccagttcctccactcagccgtgcgaagagctgactcacagcctgtgcgagcggc   240
 G  N  R  K  G  K  S  K  K  W  R  Q  M  L  Q  F  P  H  I  S  Q  C  E  E  L  R  L  S  L  E  R  D  Y  H  S  L  C  E  R  H    60 acgccattggcggcctgcttcgagagttctgtgccaggccgagccgctgtcgccttctgatgggtggccagtaagtgaccccgatgacaagcggaagg   360
 A  I  G  R  L  L  F  R  E  F  C  A  T  R  P  E  L  S  R  C  V  A  F  L  D  G  V  A  E  Y  E  V  T  P  D  D  K  R  K  A   100 catgtgggcgcacgtaacgacagaattttctgagccacagggtcctgacctcatcctgagtcccgcagctggtgacgaactgcaccagcaggtcctgcaaag   480
 C  G  R  H  V  T  Q  N  F  L  S  H  T  G  P  D  L  I  P  E  V  P  R  Q  L  V  T  N  C  T  Q  R  L  E  Q  G  P  C  K  D   140 acctttccaggaactcaccgactgactgagcgtggccccttttgccgactactgacagcatctacttcaacgtttcctcagtggaagtgctggaaaggcagc   600
 L  F  Q  E  L  T  R  L  T  H  E  Y  L  S  V  A  P  F  A  D  Y  L  D  S  I  Y  F  N  R  F  L  Q  W  K  L  E  R  Q  P   180 cagtgaccaaaacacctcagccaatacccagtccctgggcaaagtggctttggggaggtgtgcgctgccaggtgcggccacagtaagatgtatgctgcaagaagctgcaagaagaaaa   720
 V  T  K  N  T  F  R  Q  Y  R  V  L  G  K  G  G  F  G  E  V  C  A  C  Q  V  R  A  T  G  K  M  Y  A  C  K  K  L  E  K  K   220 agcggatcaagaagcggaggcgagccatgcgctgaacgagaagcagatcctgaagaaagtgaacagtaggttgtagtgagcttggctacgcctatgacaaggacgctgt   840
 R  I  K  K  R  K  G  E  A  M  A  L  N  E  K  Q  I  L  E  K  V  N  S  R  F  V  V  S  L  A  Y  A  Y  E  T  K  D  A  L  C   260 gcctggtgacactgatgaacgggggcgacctcaagttccacatctaccacatgggccaggttgcttcccgaagcgccaggggcgccgtcttttacgccgccgagatctgctgtggcctgg   960
 L  V  L  T  L  M  N  G  G  D  L  K  F  H  I  Y  H  M  G  Q  A  G  F  P  E  A  R  A  V  F  Y  A  A  E  I  C  C  G  L  E   300 aggacctgctgacactggagcgcatcgtgtacagggaccgagcctgcacatctgctgatgaccgccacactccgatctctgacctggactgtcatgtgccccgagggcc  1080
 D  L  H  R  E  R  I  V  Y  R  D  L  K  P  E  N  I  L  L  D  D  H  G  H  I  R  I  S  D  L  G  L  A  V  H  V  P  E  G  Q   340
```

```
GRK6     MELENIVANT  VLLKAREGGG  GNRKGKSKKW  RQMLQFPHIS  QCEELRLSLE   50
GRK5     ----------  ----------  -K--------  KEI-K-----  ---D--RTID
IT11     ---------S  L-----Q···  ··········  ··········  ··········
GPRK-2

GRK6     RDYHSLCERH  AIGRLLFREF  CATRPELSRC  VAFLDGVAEY  EVTPDDKRKA  100
GRK5     ---C---DKQ  P-------Q-  -E---G-ECY  IQ---S----  -----E-LGE
IT11     K--S---DKQ  P---R---Q-  -D-K-T-K-H  IE---A----  --AD-ED-SD
GPRK-2

GRK6     CGRHVTQNFL  SHTGPDLIPE  VPRQLVTNCT  QRL·EQGPCK  DLFQELTRLT  150
GRK5     K-KEIMTKY-  TPKS-VF-AQ  -GQD--SQTE  EK-·L-K---  E--SACAQSV
IT11     --LSILDR-F  NDKLAAP---  I-PDV--E-R  LG-K-EN-S-  KA-E-C--VA
GPRK-2

GRK6     HEYLSVAPFA  DYLDSIYFNR  FLQWKWLERQ  PVTKNTFRQY  RVLGKGGFGE  200
GRK5     ----RGE--H  E----MF-D-  ----------  ----------  ----------
IT11     -N--RGE--E  E-QE-S--SQ  ----------  --------H-  ----------
GPRK-2               M--H- Y---------  -I-YK---M-  ----------

GRK6     VCACQVRATG  KMYACKKLEK  KRIKKRKGEA  MALNEKQILE  KVNSRFVVSL  250
GRK5     ----------  ------R---  ----------  -S--------  ----Q---N-
IT11     ----------  --------Q-  ----------  ------R---  --Q-------
GPRK-2   ----------  ----------  ----------  -S- -V-I-----Q  -I--P---N-

GRK6     AYAYETKDAL  CLVLTLMNGG  DLKFHIYHM·  GQAGFPEARA  VFYAAEICCG  300
GRK5     ----------  -----I----  -------N-·  -NP-E-E--  L------L--
IT11     ----------  -----I----  -------NL·  -NP--D-Q--  ------L---
GPRK-2   ----------  -----I----  -------N-G  -EP--ELE--  R-----VA--

GRK6     LEDLHRERIV  YRDLKPENIL  LDDHGHIRIS  DLGLAVHVPE  GQTIKGRVGT  350
GRK5     -------NT-  ----------  ---Y------  ------KI--  -DL-R-----
IT11     ----Q-----  ----------  ---R------  -----TEI--  --RVR-----
GPRK-2   -QH--KQG--  ---C------  ------V---  ------EI--  -EMVR-----

GRK6     VGYMAPEVVK  NERYTFSPDW  WALGCLLYEM  IAGQSPFQQR  KKKIKREEVE  400
GRK5     --------LN  -Q--GL---Y  -G----I---  -E-----RG-  -E-V-----D
IT11     ---------N  --K-------  -G----I---  -Q-H---KKY  -E-V-W---D
GPRK-2   ---------ID  --K-A-----  FSF-------  -E-A--RM-  -E-V-----D
```

```
GRK6     RLVKEVPEEY SERFSPQARS LCSQLLCKDP AERLGCRGG· ·SAREVKEHP 450
GRK5     -R-L-TE-V- -HK--EE-K- I-KM--T--A KQ----QEE· ·G-A---R--
IT11     QRI-NDT--- --K--ED-K- I-RM--T-N- SK------E· ·G-AG--Q--
GPRK-2   -R---D--K- -SK-NDE-K- M-Q---A-SI KQ-----N-R M-GQD-MA--

GRK6     LFK··KLNFK RLGAGMLEPP FKPDPQAIYC KDVLDIEQFS TVKGVELEPT 500
GRK5     F-R··NM--- --E----D-- -V---R-V-- ---------- -----N-DH-
IT11     V---··DI--R --E-N----- -C---H-V-- ---------- A---IY-DTA
GPRK-2   F-HSTQ--WR --E------- -V---H-V-A ---------- -----NIDES

GRK6     DQDFYQKFAT GSVPIPWQNE MVETECFQEL NVFGLDGSVP PDLDWKGQPP 550
GRK5     -D---S--S- ---S------ -I-----K-- ----PN-TL- ---NR·NH--
IT11     -E---AR--- -C-S------ DCL-MVPS-K E-EPKQC
GPRK-2   -TN--T--N- ---S-S---- -M-----R-- ----PEECPT ---Q·INAA-

GRK6     APPKKGLLQR LFSR··QDCC GNCSDSEEEL PTRL                 576
GRK5     E--------- --K-QH-NNS KSSPS-KTSF NHHINSNHVS SNSTGSS   590
IT11                                                          500
GPRK-2   E-D-A-CFPF RRKKKQPART QPIPIP-HL- T-SHSVSSTT VES       426
```

FIG. 9B

COMPOSITIONS AND METHODS FOR MODULATING THE ACTIVITY OF G PROTEIN-COUPLED RECEPTOR KINASES GPK5 AND GRK6

INTRODUCTION

This application is a continuation-in-part of U.S. patent application Ser. No. 08/076,084 which was filed Jun. 11, 1993, now abandoned.

The invention was made in the course of research supported by the National Institutes of Health grants GM44944 and HL45964 and by a Research Supplement for Underrepresented Minorities from the National Institutes of Health. The United States Government may have certain rights in this invention.

BACKGROUND OF THE INVENTION

G protein-coupled receptors represent a diverse family of cell surface proteins that transduce the binding of extracellular ligands (hormones, neurotransmitters, odorants, light, etc.) into intracellular signalling events. G protein-coupled receptors modulate the activity of a wide variety of effector molecules including adenylyl cyclase, cGMP phosphodiesterase, phospholipase C, phospholipase A2, and $K^+$, $Na^+$ and $Ca^{++}$ channels. It has become apparent in recent years that G protein-coupled receptor kinases play a vital role in regulating receptor function by their unique ability to specifically phosphorylate activated forms of G protein-coupled receptors.

Two of the best characterized G protein-coupled receptors are the hormone responsive $\beta_2$-adrenergic receptor ($\beta_2AR$), which mediates catecholamine stimulation of adenylyl cyclase, and the visual "light receptor" rhodopsin, which mediates phototransduction in retinal rod cells. The $\beta_2AR$ and rhodopsin share many structural and functional similarities including a conserved protein topology (e.g., seven transmembrane domains) as well as an ability to specifically interact with G proteins upon activation. The similarities between these receptors also extend to mechanisms involved in receptor regulation. In both of these systems, a rapid loss of receptor responsiveness occurs following activation. This rapid activation-dependent loss of responsiveness or desensitization is promoted by phosphorylation of the receptor. This phosphorylation is mediated by protein kinases that have the unique ability to recognize and phosphorylate their receptor substrates only when they are in their active conformations, i.e., when they have been stimulated and/or occupied by appropriate agonist ligands. The β-adrenergic receptor kinase (βARK) and rhodopsin kinase have been identified as kinases involved in the agonist-specific phosphorylation of the $\beta_2AR$ and rhodopsin, respectively. The subsequent uncoupling of the receptor and G protein is then mediated by arrestin proteins that specifically bind to the phosphorylated and activated form of the receptor. Additional lines of evidence suggest that other G protein-coupled receptors may also be regulated by similar mechanisms. These receptors include the m2 muscarinic cholinergic and α2-adrenergic receptors, which inhibit adenylyl cyclase; the α mating factor receptor of the yeast *Saccharomyces cerevisiae* and the chemotactic cAMP receptor of the slime mold *Dictyostelium discoideum*.

Several lines of evidence suggest that βARK may have a broad substrate specificity and thus serve as a general G protein-coupled receptor kinase. First, direct phosphorylation studies have demonstrated that βARK not only phosphorylates the $\beta_2AR$ to a high stoichiometry, but also can phosphorylate the α2-adrenergic, the m2 muscarinic cholinergic and the substance P receptors. In addition, several agents appear to promote an increase in membrane-associated βARK activity. These include β-agonists, prostaglandin E1, somatostatin, and platelet activating factor, suggesting the involvement of βARK in the regulation of these receptors. Moreover, a growing body of evidence suggests that βARK and rhodopsin kinase are members of a multigene family.

Structural information on the G protein-coupled receptor kinase (GRK) family was initially provided by the isolation of a cDNA encoding bovine βARK [Benovic, J. L., DeBlasi, A., Stone, W. C., Caron, M. G., and Lefkowitz, R. J., 1989 *Science*, 246:235–246]. βARK is a protein of 689 amino acids (79.6 kD) containing a central protein kinase catalytic domain flanked by large amino and carboxyl terminal domains. Additional members of the GRK family were subsequently cloned including bovine βARK2 [Benovic, J. L., Onorato, J. J., Ariza, J. L., Stone, W. C., Lohse, M., Jenkins, N. A., Gilbert, D. J., Copeland, N. G., Caron, M. G. and Lefkowitz, R. J., 1991 *J. Biol. Chem.*, 266:14939–14946], bovine rhodopsin kinase [Lorenz, W., Inglese, J., Palczewski, K., Onorato, J. J., Caron, M. G. andLefkowitz, R. J., 1991 *Proc. Natl. Acad. Sci. USA*, 88:8715–8719], Drosophila kinases GPRK-1 and GPRK-2 [Cassill, J. A., Whitney, M., Joazeiro, C. A. P., Becker, A., and Zucker, C. S., 1991 *Proc. Natl. Acad. Sci. USA*, 88:11067–11070], and the recently identified human IT11 [Ambrose, C., James, M., Barnes, G., Lin, C., Bates, G., Altherr, M., Duyao, M., Groot, N., Church, D., Wasmuth, J. J., Lehrach, H., Housman, D., Buckler, A., Gusella, J. F., and MacDonald, M. E., 1992 *Human Mol. Genet.*, 1:697–703]. βARK2 and Drosophila GPRK-1 appear to be the most similar to βARK with amino acid identities of 84% and 64%, respectively. In contrast, rhodopsin kinase, IT11, and Drosophila GPRK-2 have significantly lower homology with βARK (35–406 amino acid identity). Common features of these kinases include a centrally localized catalytic domain of approximately 240 amino acids which shares significant amino acid identity (46 to 95%), an N-terminal domain of 161–197 amino acids (except for GPRK-2), and a variable length C-terminal domain of 100–263 amino acids.

The tremendous diversity in the G protein-coupled receptor family suggested that there may well be other GRK members. This has, in fact, been found to be the case. In the present invention, two additional members of the GRK gene family have been identified, GRK5 and GRK6; these cDNAs have now been cloned, expressed and characterized.

SUMMARY OF THE INVENTION

G protein-coupled receptor kinases (GRK) play an important role in phosphorylating and regulating the activity of G protein-coupled receptors. Complementary DNAs (cDNAs) that encode two novel members of the G protein-coupled receptor kinase family are provided in the present invention. These cDNAS (SEQ ID NO: 1 and SEQ Id NO: 2, respectively) encode GRK5 (590 amino acids; SEQ ID NO:5) and GRK6 (576 amino acids; SEQ ID NO:6) which represent two new members of the GRK family that have distinct tissue distribution and substrate specificity. These kinases have been overexpressed in Sf9 insect cells, purified and characterized. Using the purified kinases, it has been demonstrated that heparin is a potent inhibitor of GRK5 ($IC_{50}$~1 nM) and a good inhibitor of GRK6 ($IC_{50}$~15 nM). These results indicate that specific inhibitors of these two kinases can be identified.

The GRK5 and GRK6 cDNAS can be expressed, purified and further characterized with regard to their substrate specificity. The availability of the cDNAs will also enable the generation of reagents to block the activity of the endogenous kinases. These include dominant negative mutations which involves mutating a critical lysine residue in the kinase to arginine. This results in a protein kinase which can still bind to its receptor substrate but can no longer transfer a phosphate group to the receptor. Thus, the mutant kinase can block the ability of the endogenous kinase to phosphorylate a given receptor and thereby block desensitization. An alternative strategy for blocking the activity of the endogenous kinase involves the use of antisense oligonucleotides or stably transfected antisense constructs to block expression of the kinase. This will generate a cell with a reduced ability to desensitize to various agents. Expression of GRK5 and GRK6 will also allow screening for specific inhibitors of these two kinases. It has been demonstrated that heparin is a potent inhibitor of GRK5 and a good inhibitor of GRK6. Inhibitors are identified and then utilized to specifically block the activity of GRK5 or GRK6, and thus inhibit receptor desensitization. Specific inhibitors of these kinases may be used therapeutically to either directly modulate the activity of a given receptor (by blocking endogenous desensitization of that receptor) or by augmenting the ability of a given therapeutic agent to stimulate a given receptor (again by blocking desensitization). Alternatively, a specific activator of GRK5 or GRK6 could be used to stimulate the desensitization or turn-off of an overactive (e.g., oncogenic) receptor.

DESCRIPTION OF THE DRAWINGS

FIG. 2 is a nucleotide and deduced amino acid sequence of human GRK5. The nucleotide sequence of the full length clone pGRK5 is shown. The nucleotides are numbered on the right hand side beginning at the 5' end and ending at the 3' end of the clone pGRK5. The predicted amino acid sequence is numbered on the right hand side just below the nucleotide sequence, beginning at the first in frame ATG (bp 221) and ending just before the first in frame stop codon (bp 1990). The predicted initiator methionine is flanked by the nucleotide sequence TCAATGG. IUPAC single letter abbreviations for amino acids are used.

FIG. 7 is a nucleotide and deduced amino acid sequence of human GRK6. The composite nucleotide sequence from several of the GRK6 clones is shown. The nucleotides are numbered on the right hand side beginning with the 5' end of clone pGRK6-hh2 and ending at the 3' end of clone pGRK6-hb13. The amino acid sequence of GRK6 is numbered just below the nucleotide sequence and begins with the first ATG in the nucleotide sequence (bp 63) and ends just before the first in frame stop codon (bp 1790). The GXGXXGX$_{-16}$K found in all protein kinases is shown in bold type as is the sequence DLG, which is highly conserved in the GRK family. IUPAC single letter abbreviations for amino acids are used.

FIG. 9 shows the alignment of the amino acid sequences of GRK6 with GRK5, IT11 and GPRK-2. The PILEUP program in the GCG software was used to align and compare the amino acid sequences of human GRK6, GRK5, IT11 and Drosophila GPRK-2. Only the amino acids that are different from GRK6 are shown. Identical residues are indicated as a dash (-) while gaps produced by the alignment are shown as a period (.). The amino acid sequence is numbered on the right. Overall, GRK6, GRK5, IT11 and GPRK-2 are 576, 590, 500 and 426 amino acids in length, respectively.

DETAILED DESCRIPTION OF THE INVENTION

To identify additional members of the GRK family, degenerate oligonucleotide primers were designed to encode several highly conserved amino acid stretches found in all of the GRKs. These oligonucleotides were then used as primers in a polymerase chain reaction (PCR) using template DNA prepared from a human heart cDNA library.

GRK5

One set of primers yielded a PCR product of the expected size (~450 bp) as assessed by electrophoresis on a 2% agarose gel. The 450 bp DNA product was then restriction digested with EcoRI and HindIII (sites present in the two PCR primers), subcloned into EcoRI/HindIII digested pBluescript KS and sequenced using T3 and T7 primers. Of the 20 clones sequenced, 13 were identical and had 54% amino acid identity with bovine βARK, 64% identity with bovine rhodopsin kinase and 83% identity with Drosophila GPRK-2. This PCR product also encoded the amino acid sequence Asp Leu Gly (DLG), a sequence that is highly conserved in the GRK family. The other 7 clones sequenced had no appreciable homology with the GRK family.

Figure 1:
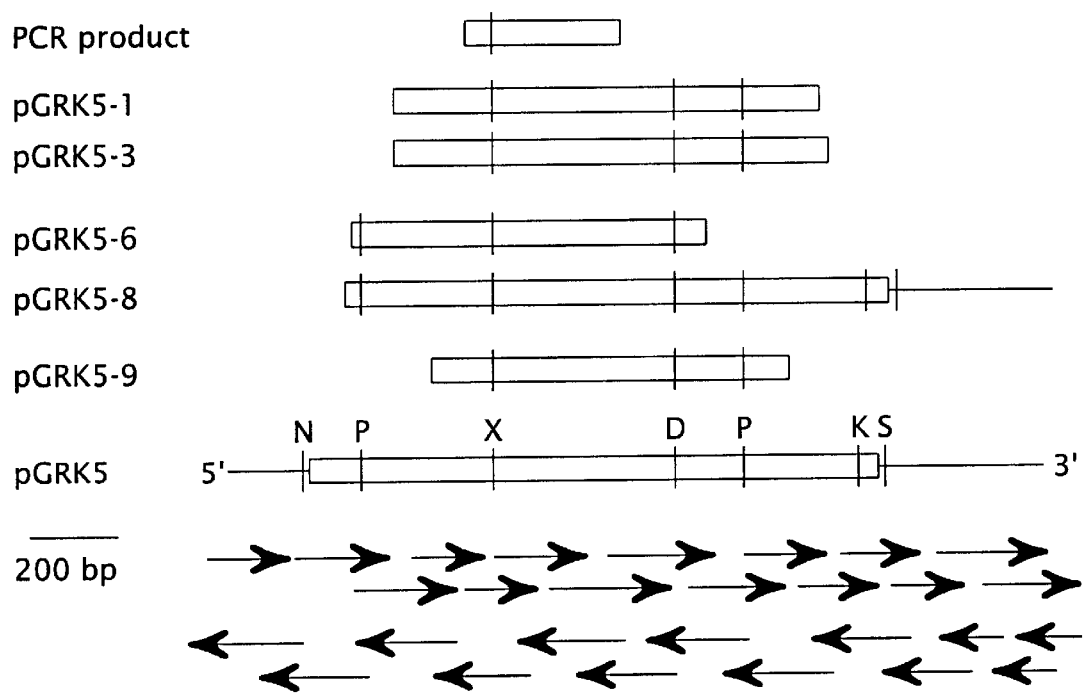
FIG. 1 is a restriction map and sequencing strategy for the GRK5 clones. The restriction sites on the human heart pGRK5 clones are indicated for the enzymes NaeI (N), PstI (P), XhoI (X), DraII (D), KpnI (K) and SmaI (S). Clone PGRK5 has an open reading frame of 1770 bp starting from the first in frame ATG. DNA sequencing was performed by the dideoxynucleotide chain termination technique. The extent and direction of the sequence reactions are shown by the arrows. The open reading frame is indicated as an open rectangle while untranslated sequences are indicated as a line.
Figure 2A:
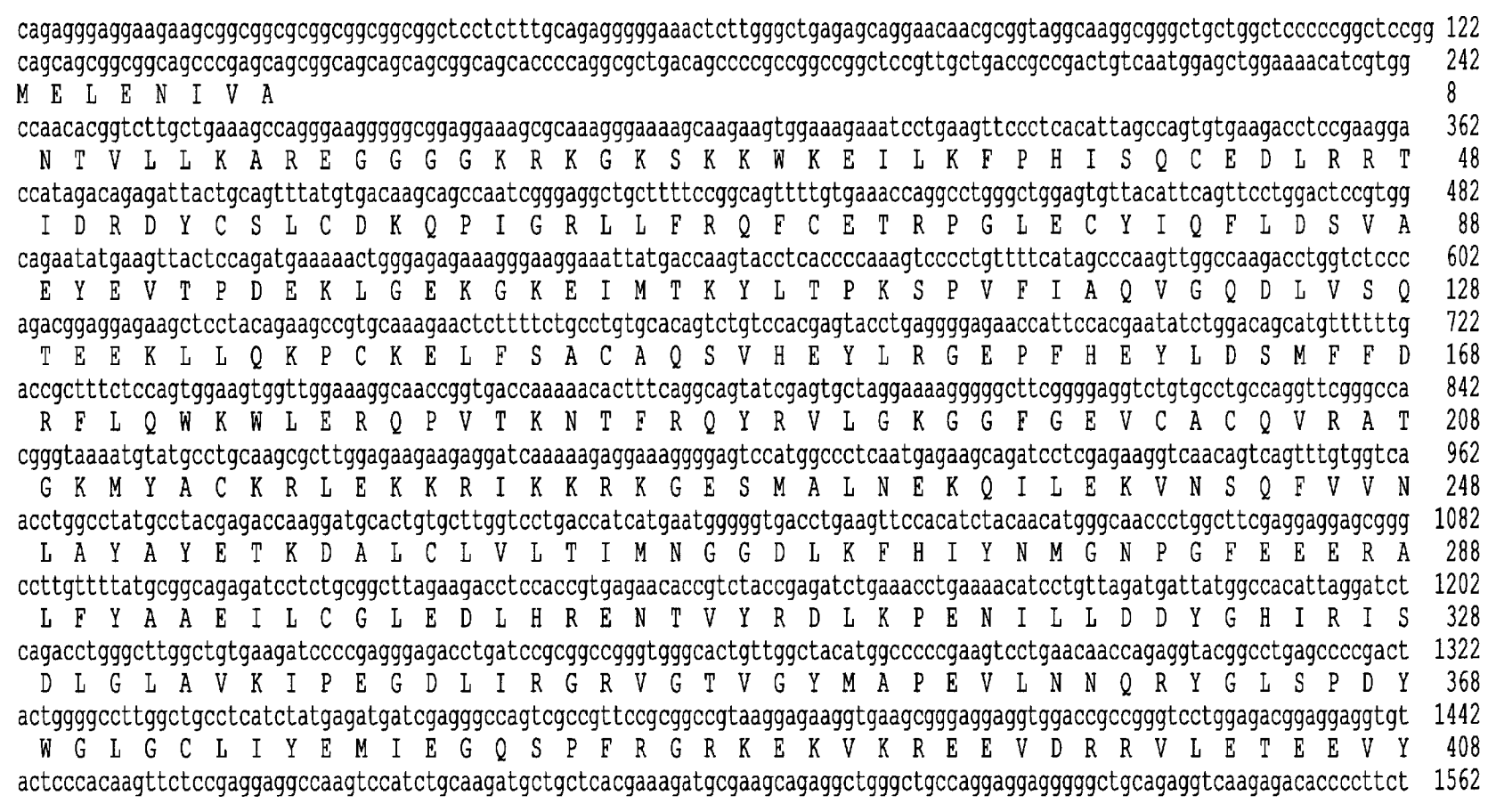

The GRK-related PCR product was then labeled with [$^{32}$P] dCTP by random priming and used as a probe to screen the human heart cDNA library. Six different cDNA clones were isolated by this method. The relative lengths, partial restriction maps and sequencing strategy for these clones are shown in FIG. 1. Of the six clones isolated, pGRK5-1 and pGRK5-3 encode an ~1.5 Kb ORF fragment while pGRK5-6 and pGRK5-9 encode ~1.1 Kb of the ORF. The clone pGRK5-8 is ~2.2 Kb in length and appears to encode the 3' end of the ORF as well as the entire 3' untranslated sequence. The full length clone pGRK5 is 2.55 Kb in length and contains an open reading frame of 1770 bp which is flanked by 220 bp of 5' untranslated and 567 bp of 3' untranslated sequence. The 5' untranslated sequence is relatively GC rich (73%) while the 3' untranslated sequence ends with a poly A tail. While pGRK5 does not have a good Kozak consensus sequence for translation initiation (TCAATGG instead of ACCATGG), the comparison of GRK5 with the other known GRKs helped to determine the initiator methionine. The predicted open reading frame, beginning at the first in frame ATG and ending at the first in frame stop codon (SEQ ID NO: 1), encodes a protein of 590 amino acids (FIG. 2) comprising SEQ ID NO: 5 (GenBank accession number L15388).

Figure 3:
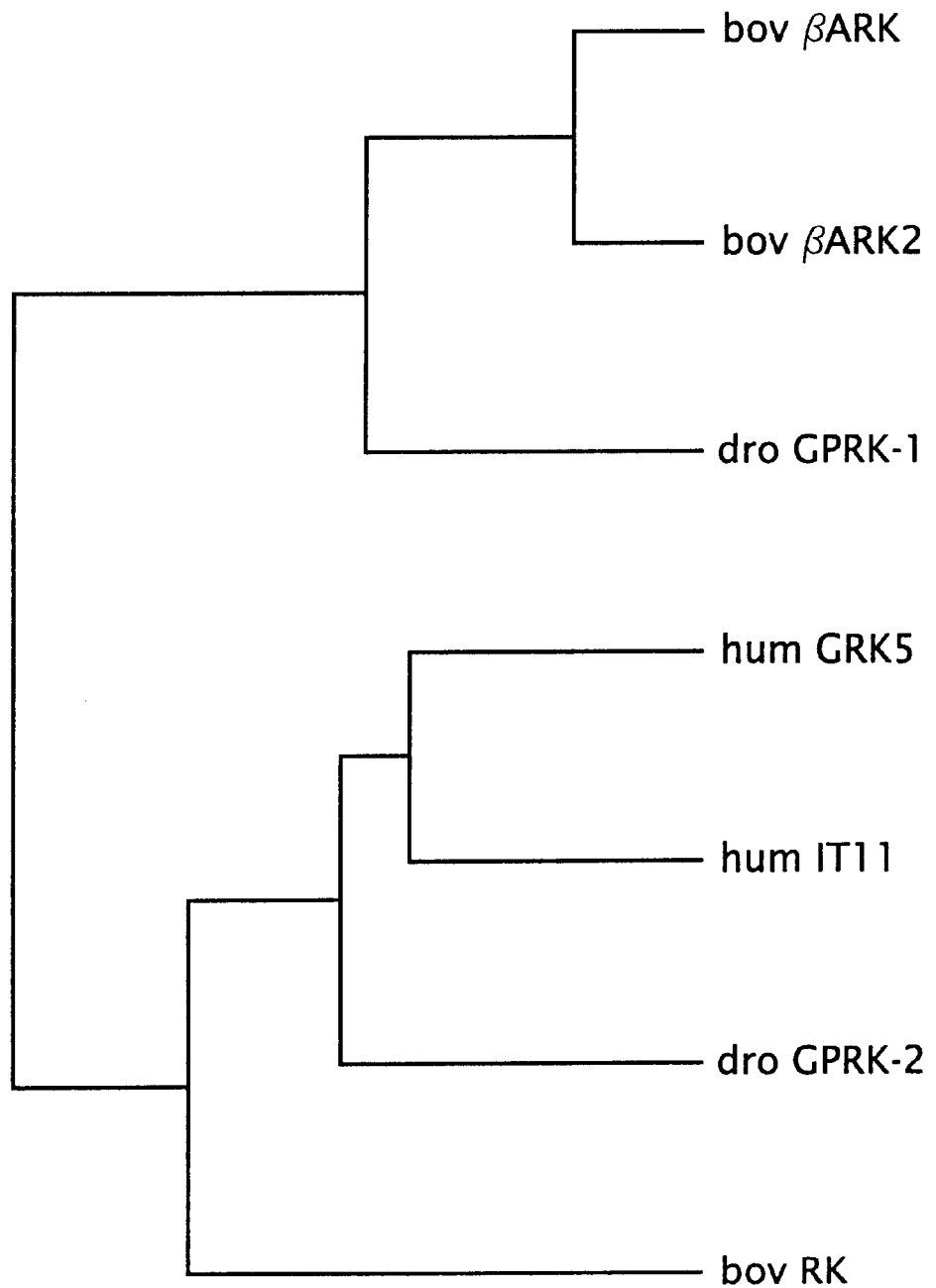
FIG. 3 is a comparison of the amino acid sequence of GRKS with related GRKs by dendogram analysis. The PILEUP program in the Wisconsin Genetics Computer Group software was used to align and compare the amino acid sequences of human GRK5 and IT11, bovine βARK, βARK2 and rhodopsin kinase and Drosophila GPRK-1 and GPRK-2. The overall amino acid identities of GRK5 with the other GRKs are 69% with human IT11, 71% with Drosophila GPRK-2, 47% with bovine rhodopsin kinase, 36% with bovine βARK and βARK2, and 35% with Drosophila GPRK-1. The PILEUP program uses a progressive pairwise alignment.

The predicted molecular weight of GRK5 is 67.6 kDa, with a predicted pI of 8.75. GRK5 contains a centrally located protein kinase catalytic domain of 238 amino acids flanked by N-terminal and C-terminal regions of 193 and 159 amino acids, respectively. Comparison of the amino acid sequence of GRK5 with other known GRKs reveals a high degree of overall homology, particularly in the catalytic domain. Construction of a phylogenetic tree of all the known GRKs demonstrates that GRK5 is most closely related to human IT11 and that GRK5, IT11, GPRK-2 and rhodopsin kinase form a distinct branch of the GRK family as compared to βARK, βARK2 and GPRK-1 (FIG. 3). GRK5 has an overall 69% amino acid identity and 82% similarity with human IT11. The major differences between these proteins include a 33 amino acid gap in IT11 near the N-terminus, a divergent stretch in the central portion of the N-terminus (only 19% identity and 47% similarity from amino acids 97–149), and a significant difference in the length of the C-terminus (100 and 159 amino acids for IT11 and GRK5, respectively). GRK5 also has high homology with Drosophila GPRK-2, with 71% amino acid identity and 82% similarity. However, GPRK-2 has a very short N-terminal domain (28 amino acids) compared to all other GRKs (161–197 amino acids). GRK5 also has higher homology to rhodopsin kinase (68% amino acid similarity) than to βARK (58% similarity), both in amino acid identity and size. While the functions of the N-terminal and C-terminal domains of these kinases are largely unknown, the carboxyl terminal tail of rhodopsin kinase is farnesylated, a post-translational modification that appears to be important for its translocation to the disc membrane. By comparison, the C-terminal domain of βARK appears to interact with G protein βγ subunits. Overall, GRK5, IT11, rhodopsin kinase and GPRK-2 have significantly shorter C-terminal tails as compared to βARK, βARK2 and GPRK-1.

Figure 4:
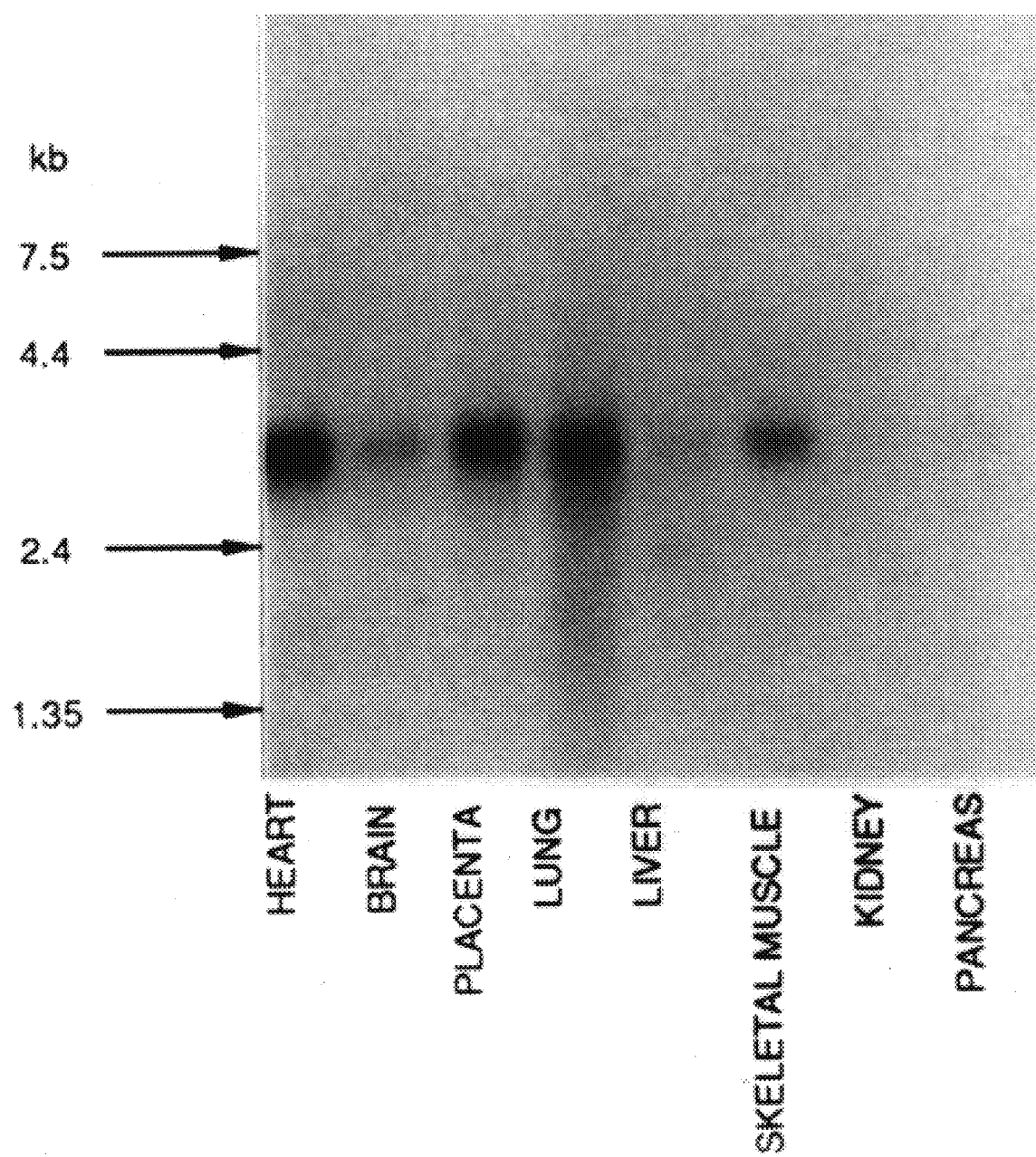
FIG. 4 is a Northern blot analysis of human mRNA from various tissues. Two tg of poly A⁺ RNA from human heart, brain, placenta, lung, liver, skeletal muscle, kidney and pancreas on a Multiple Tissue Northern blot was hybridized with a 1157 bp PstI ORF fragment from the clone pGRK5. The blot was washed in 0.1×SSC, 0.1% SDS at 60° C. followed by autoradiography at −80° C. for 24 hours.

The tissue distribution of GRK5 was analyzed by Northern hybridization using a human multiple tissue Northern blot containing 2 μg of poly A$^+$ RNA from eight different human tissues. A randomly primed 1157 bp PstI ORF fragment from pGRK5 was labeled with [$^{32}$P] dCTP and used as a probe. This revealed a message of 3.0 Kb with highest levels in the human heart, placenta, lung>skeletal muscle>brain, liver, pancreas>kidney (FIG. 4). This tissue distribution is in contrast to βARK, which has a message of 3.8 Kb, with highest levels in the brain, skeletal muscle>pancreas>heart, lung, placenta, kidney>liver. Previous studies have demonstrated that IT11 has highest message levels in testis but is also found at low levels in a wide variety of tissues. Drosophila GPRK-2 also appears to be expressed in a variety of tissues. In contrast, rhodopsin kinase is more specifically localized in the rod outer segments of the retina, with low levels also observed in the pineal gland. The rather unique tissue distribution of GRK5, as compared to the other GRKs, suggests that GRK5 likely has a unique substrate specificity and physiological role within the cell.

Figure 5A:
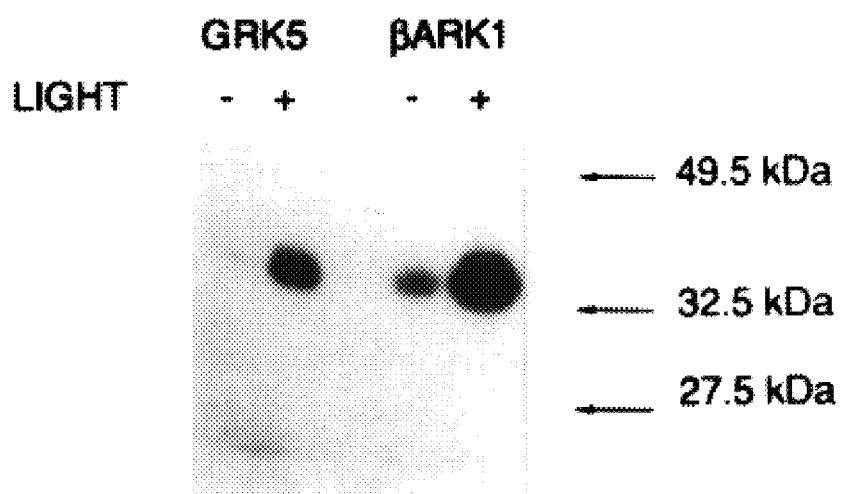
FIG. 5 shows expression of GRK5 in Sf9 Insect Cells. A. GRK5- and βARK-containing recombinant baculoviruses were used to infect a monolayer of Sf9 cells. Following a 48 hour infection, the cells were harvested, lysed in 1.5 ml of buffer and then centrifuged at 40,000×g for 20 minutes. The supernatants were then used to phosphorylate urea treated ROS either in the presence or absence of room light. The reactions were stopped by the addition of 50 μl of SDS sample buffer and the samples were then electrophoresed on a 10% SDS polyacrylamide gel. The gel was dried and autoradiographed for 30 minutes at room temperature and the rhodopsin bands were then cut and counted. The level of light-dependent rhodopsin phosphorylation in this experiment was 7 pmol/min/mg using the supernatant from wild type Sf9 cells, 1120 pmol/min/mg by Sf9 cells expressing GRK5, and 2470 pmol/min/mg by Sf9 cells expressing βARK. B. The Sf9 cell supernatants were also used to phosphorylate urea treated ROS in the presence or absence of G protein βγ subunits. The reactions were stopped, electrophoresed and autoradiographed for 120 minutes at room temperature.

To initially characterize the activity of GRK5, the ORF from pGRK5 was excised by restriction digestion with NaeI and SmaI and then subcloned into the baculovirus expression vector pBacPAK1. Viral DNA and the pBacPAK-GRK5 construct were then cotransfected into Sf9 cells to obtain an isolated recombinant virus. The recombinant virus was amplified and then used to infect a monolayer of Sf9 cells. As shown in FIG. 5A, GRK5 expressed in Sf9 cells phosphorylates rhodopsin in a light dependent manner. The ability of GRK5 to phosphorylate rhodopsin was also compared to βARK (FIG. 5A, right). Overall, while both GRK5 and βARK phosphorylated rhodopsin well above the basal "ARK-like" activity observed in Sf9 cells, GRK5 was less active than βARK at phosphorylating rhodopsin. When the supernatant fractions from the GRK5 and βARK infected cells were analyzed by polyacrylamide gel electrophoresis and Coomassie Blue staining, comparable levels of GRK5 and βARK were observed. This suggests that the difference in activity is not due to a difference in the expression levels of the two kinases. Purified GRK5 exhibited several properties similar to many other protein kinases including a preferential requirement for $Mg^{2+}$ as the divalent cation, a pH optimum of 5.5 to 7.5, and a Km for ATP of 24 $\mu$M.

Figure 5B:
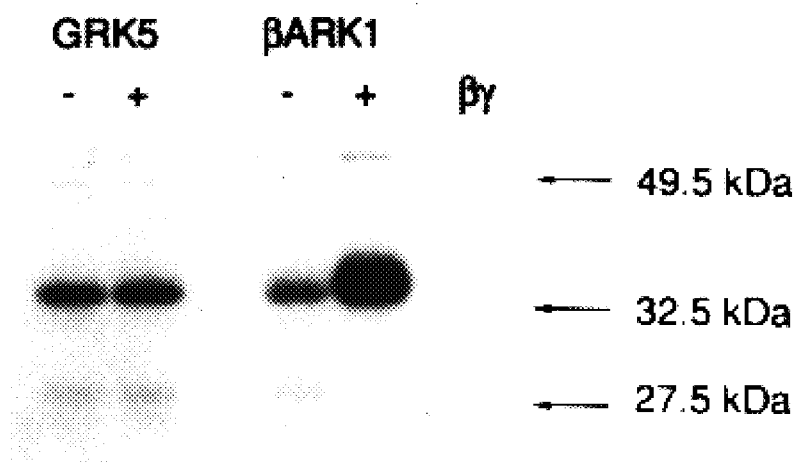

The two most extensively studied GRKs, rhodopsin kinase and βARK, appear to be regulated by different mechanisms. Farnesylation of rhodopsin kinase at its C-terminus appears to be important for the translocation of rhodopsin kinase to the disc membrane. βARK, on the other hand, may associate with membranes via its specific interaction with G protein βγ subunits. Since GRK5 does not contain a consensus sequence for isoprenylation (CAAX) at its C-terminus, the ability of G protein βγ subunits to modulate the activity of GRK5 was tested. It was found that βARK is significantly activated in the presence of G protein βγ subunits (FIG. 5B, right). In contrast, the ability of GRK5 to phosphorylate rhodopsin is not affected by G protein βγ subunits (FIG. 5B, left). In addition, unlike βARK, GRK5 phosphorylation appears to be biphasic suggesting that there may be a primary site or sites that are rapidly phosphorylated by GRK5 followed by slower phosphorylation of additional sites. Thus, GRK5 appears to utilize a novel mechanism of regulation and/or cellular localization as compared to βARK and rhodopsin kinase.

GRK5 has been found to have a complex substrate specificity that is not defined simply by the presence of absence of acidic or basic residues in the vicinity of a serine or threonine. Previous peptide phosphorylation studies revealed that βARK preferentially phosphorylates Ser/Thr residues in an acidic environment, while rhodopsin kinase phosphorylates peptides with acidic amino acids carboxyl-terminal to the Ser/Thr. A number of peptides tested in these experiments were also found to be substrates for GRK5. However, in contrast to βARK and rhodopsin kinase, GRK5 was found to prefer peptides that do not contain acidic amino acids in the vicinity of a serine. The kinetic parameters for the peptides tested indicate that the presence of acidic residues predominantly decreases the rate of the phosphorylation rather than the affinity of GRK5 for these peptides. In contrast, results obtained using several general protein kinase substrates have shown that the acidic proteins casein and phosvitin are weakly phosphorylated by GRK5 while the basic histones were not phosphorylated by GRK5.

The modulation of GRK5 activity by polyanions also revealed several differences as compared to βARK and rhodopsin kinase. Although heparin and dextran sulfate have been identified as the most potent inhibitors of βARK with $IC_{50}$s of 150–2800 nm, these compounds are >150-fold more potent at inhibiting GRK5 ($IC_{50}$ of ~1 nM and ~0.6 nM, respectively). Heparin is also a potent inhibitor of casein kinase II ($IC_{50}$ of ~20 to 60 nM); however, it is only a weak inhibitor of rhodopsin kinase ($IC_{50}$ of ~200 $\mu$M). Several other polyanions such as polyaspartic and polyglutamic acid have also been found to be much more potent inhibitors (16–80 fold) of GRK5 as compared to βARK. This tremendous variance in the ability of polyanions to inhibit different members of the GRK family indicates that specific inhibitors of these kinases can be found. Two other compounds were also tested for their ability to inhibit GRK5. H-7, a potent inhibitor of protein kinase C and the cAMP- and cGMP-dependent protein kinases, was found to be a weak inhibitor of GRK5 ($IC_{50}$ of ~170 $\mu$M). Similarly, NaCl also appears to inhibit the activity of GRK5 with an $IC_{50}$ of ~60 mM, similar to the inhibition of βARK by NaCl.

Since polyanions were potent inhibitors of GRK5, the effects of polycations on GRK5 activity were also studied. While polycations such as spermine, spermidine and polylysine are weak inhibitors of βARK, they are activators of rhodopsin kinase and casein kinase. Previous studies have shown that polyamines like spermine and spermidine activate casein kinase II 2–3 fold and may serve as physiological modulators of this kinase in reticulocytes. GRK5 is also significantly activated by the polycations polylysine, spermine, and spermidine. Furthermore, the extent of the activation of GRK5 by these polycations appears to be proportional to their charge, since optimal concentrations of spermidine, which contains 3 positive charges, activates GRK5 ~1.5-fold, while spermine, which contains 4 positive charges, activates GRK5 ~1.8-fold. Polylysine, a 14–16 amino acid peptide, is the most potent activator of GRK5 among the compounds tested, promoting a ~2.6-fold activation at an optimal concentration of 10 $\mu$M. While polycations do not activate βARK, at lower concentrations they are able to partially reverse the inhibition of βARK by heparin, most likely by directly binding to heparin and thereby preventing its inhibition. A similar phenomenon was observed for GRK5, where spermine, spermidine, and polylysine effectively reversed the ability of heparin to inhibit GRK5. Accordingly, it is believed that in vivo polyamines or polycationic surfaces may act as physiological modulators of GRK5.

Further analysis of GRK5 has revealed that it undergoes rapid intramolecular autophosphorylation reaching a stoichiometry of ~1.5 mol of phosphate/mol of kinase after ~15 minutes. Among the GRKs identified to date, only rhodopsin kinase has been previously demonstrated to undergo extensive autophosphorylation. The characteristics of GRK5 autophosphorylation appear similar to those of receptor phosphorylation of GRK5, since both have a similar Km for ATP (21 and 24 $\mu$M, respectively) and both are inhibited by NaCl ($IC_{50}$ values of ~70 and 58 mM, respectively). However, heparin, a potent inhibitor of GRK5-mediated receptor phosphorylation, does not inhibit autophosphorylation, even at a concentration of 10 $\mu$M. Testing of additional compounds showed that crude soybean phosphatidylcholine liposomes activate the autophosphorylation. GRK5 was demonstrated to directly bind to the phospholipids, thus, indicating that the interaction between GRK5 and phosphatidylcholine liposomes may serve as a mechanism for promoting GRKS association with membranes. This phospholipid-stimulated autophosphorylation of GRK5 is believed to provide a mechanism for both activation of kinase, as well as a potential mechanism for the in vivo targeting of GRK5 to its receptor substrates.

GRK6

Figure 6:
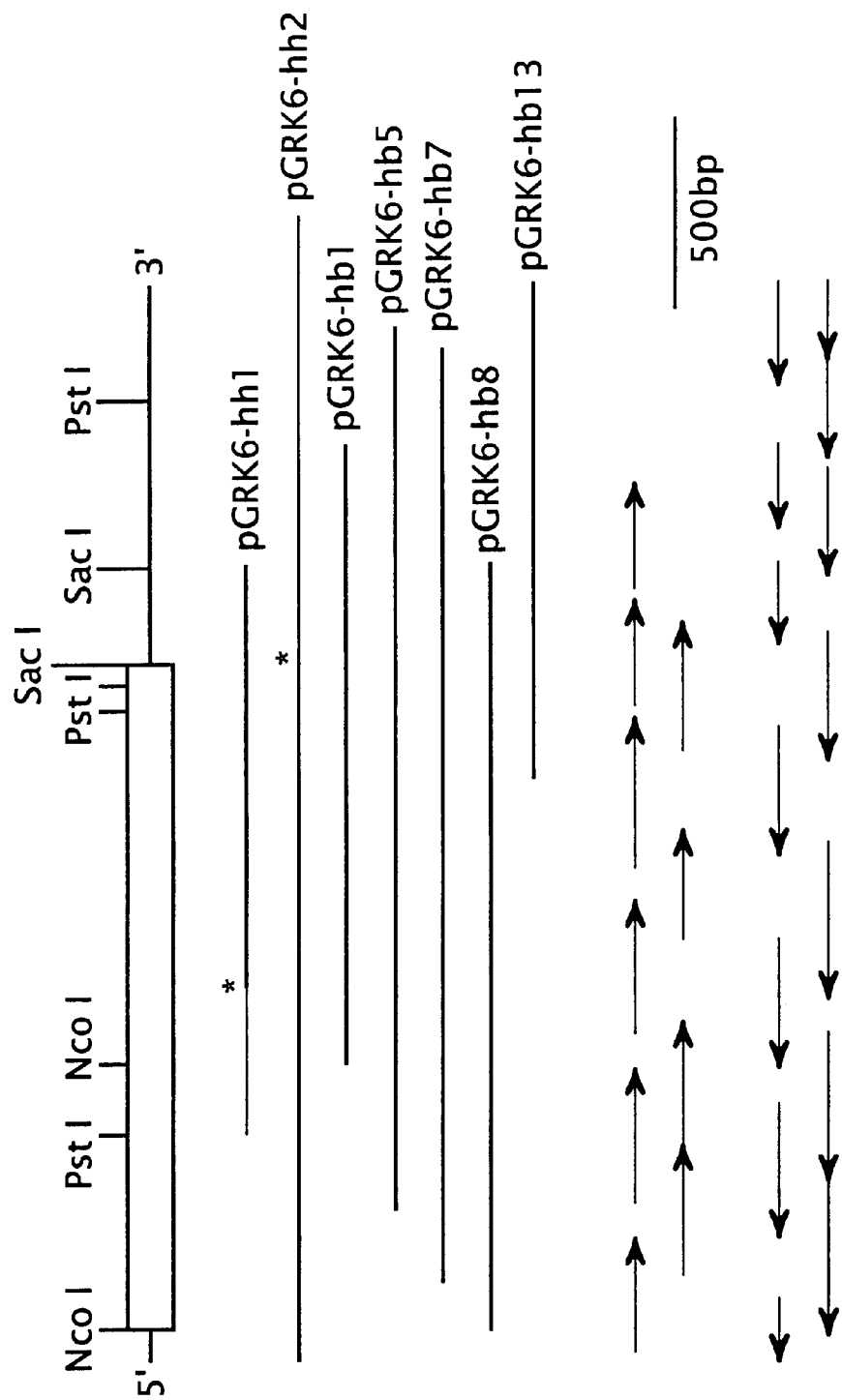
FIG. 6 is a restriction map and sequencing strategy for the GRK6 clones. The restriction sites on seven of the human heart and brain cDNA clones are shown for SacI, PstI and NcoI. DNA sequencing was performed by the dideoxynucleotide chain termination method. The extent and direction of the sequence reactions are shown by the arrows. The pGRK6-hh1, -hh2 and -hb8 clones were sequenced in their entirety while the other clones were restriction mapped and partially sequenced. Sequence divergence in the GRK6-hh1 and -hh2 clones compared with the other clones is denoted by an asterisk (*) and thin line.

To identify additional GRK cDNAs, a randomly primed, human heart cDNA library was screened with catalytic domain fragments from the bovine βARK and βARK2 cDNAs by low stringency hybridization. This procedure identified one clone which hybridized at low stringency but not high stringency (washed off between 0.5× and 0.2×SSC at 60° C.). A number of other clones which hybridized at high stringency (0.1×SSC at 60° C.) were presumed to be βARK or βARK2 and were not pursued further. The one low stringency clone, termed pGRK6-hh1, was ~1.6 kb in length and was restriction mapped and sequenced in its entirety (FIG. 6). This clone contained an ~840 bp stretch that had significant homology with the GRKs and, in particular, with IT11 and GRK5. However, the homology of pGRK6-hh1 with the other GRKs ended abruptly within the catalytic domain (FIG. 6) suggesting an incomplete clone. Therefore, a 0.6 kb open reading frame (ORF) DraII fragment from pGRK6-hh1 was isolated and labeled and used to rescreen the human heart cDNA library. This yielded one additional clone, pGRK6-hh2, that was also isolated, restriction mapped and sequenced (FIG. 6). This clone was ~3 kb in length and appeared to contain the entire ORF for GRK6. However, the sequence of the hh2 clone diverged from hh1 near the 3' end of the ORF (marked by an * in FIG. 6). Since this sequence difference lies near an EcoRI site in the hh2 clone that is not found in hh1, the hh2 clone may have resulted from ligation of the GRK6 cDNA with another cDNA during the preparation of the human heart cDNA library. To verify the sequence of GRK6, a human brain cDNA library was screened using a 1780 bp EcoRI fragment from pGRK6-hh2. This resulted in the isolation of 13 additional high stringency clones which were restriction mapped and either partially or completely sequenced. The restriction maps and sequencing strategy for several of the GRK6 clones are depicted in FIG. 6.

Figure 7B:
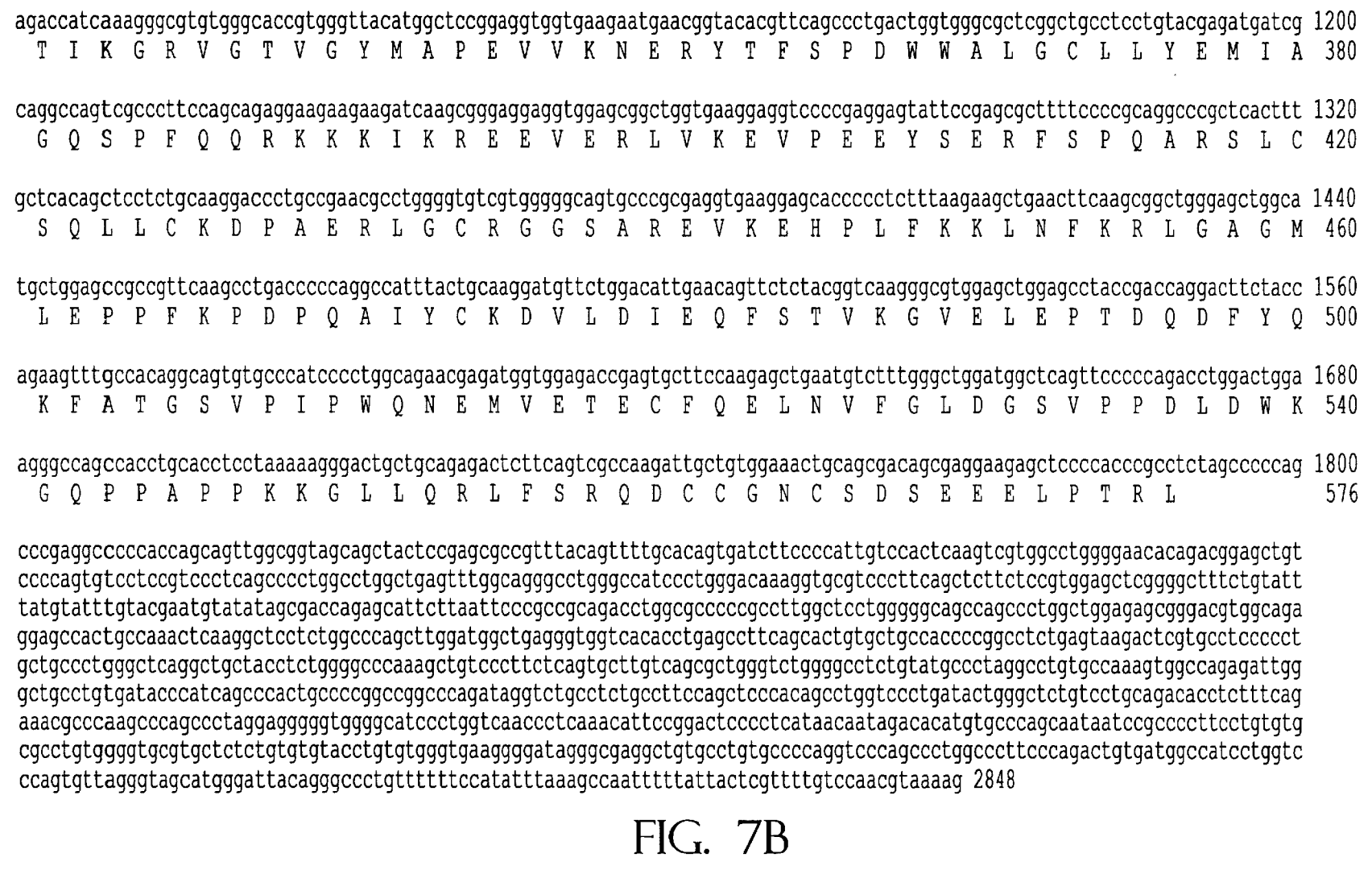

Overall, these overlapping clones yielded 2848 bp of nucleotide sequence (SEQ ID NO: 2) with an open reading frame of 1728 bp flanked by 62 bp of 5' untranslated and 1058 bp of 3' untranslated sequence (FIG. 7). The ORF of pGRK6 encodes a protein of 576 amino acids with a predicted molecular mass of 65,968 daltons comprising SEQ ID NO: 6 (GenBank accession number L16862). The first ATG in this sequence may serve as the initiation site for translation since it has a good Kozak consensus sequence and is preceded by a GC-rich region (89% in the first 62 bp), a feature common to all of the GRKs. This predicted initiator methionine and N-terminal region of GRK6 also has significant homology with several of the other GRKs. The overall topology of GRK6 suggests an N-terminal domain of 192 amino acids, a central catalytic domain of 239 amino acids and a C-terminal domain of 145 amino acids. While the N-terminal and catalytic domains of GRK6 are similar in size to those of βARK (197 and 239 amino acids), its C-terminus is significantly shorter than that of βARK (253 amino acids). The catalytic domain of GRK6 contains the highly conserved $GXGXXGX_{-16}K$ stretch as well as all of the other amino acids that are highly conserved in protein kinases. GRK6 also contains the sequence Asp Leu Gly (residues 329–331) within the catalytic domain, a sequence unique to the GRK family (other protein kinases contain Asp Phe Gly).

Figure 8:
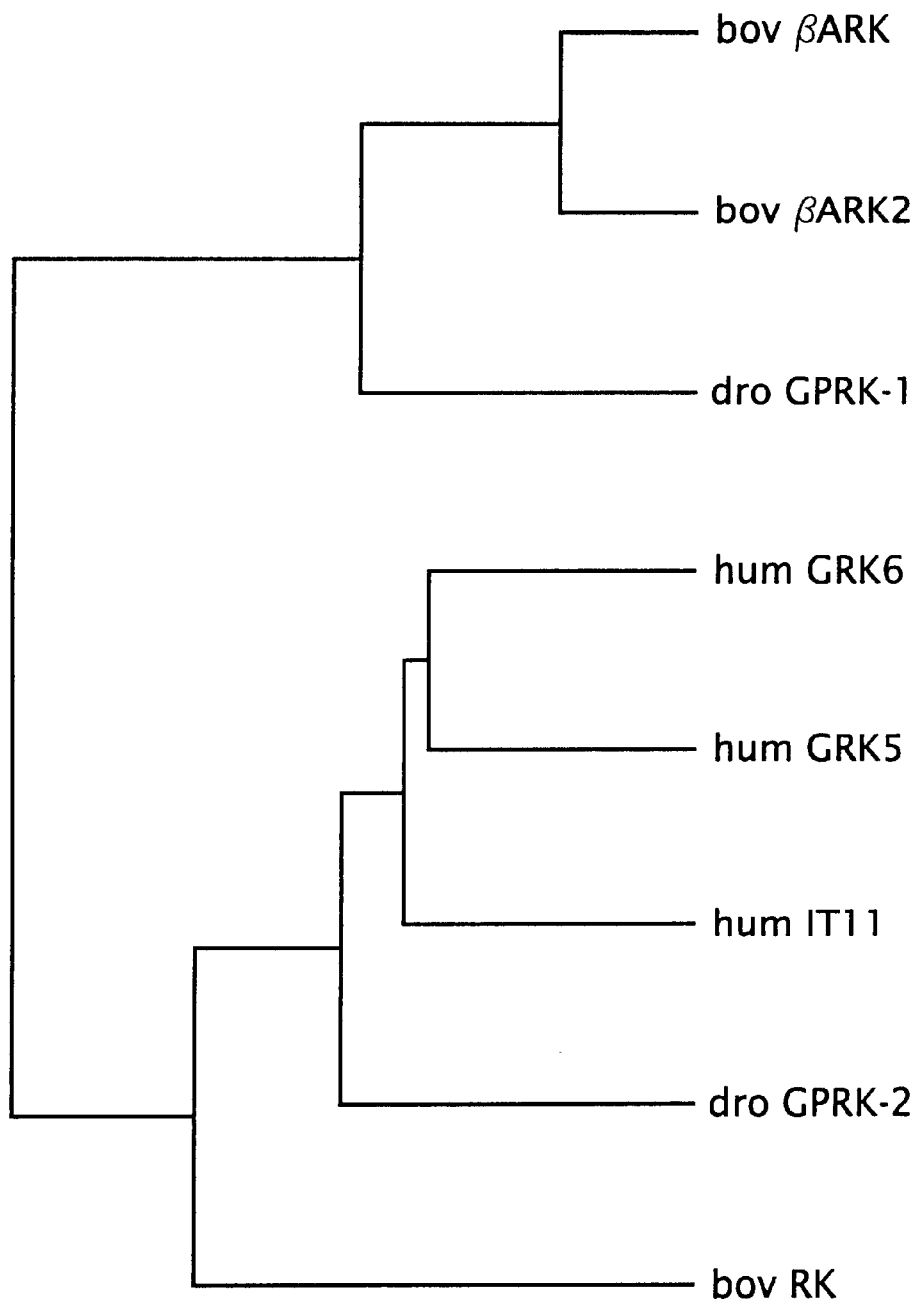
FIG. 8 is a comparison of the amino acid sequence of human GRK6 with related GRKs by dendogram analysis. The PILEUP program in the Wisconsin Genetics Computer Group (GCG) software was used to align and compare the amino acid sequences of human GRK6, GRK5, IT11, bovine βARK, βARK2, rhodopsin kinase and Drosophila GPRK-1 and GPRK-2. The overall amino acid identities of GRK6 with the other kinases are 70.1% (human GRK5), 68.56 (human IT11), 66.7% (Drosophila GPRK-2), 47.1% (bovine rhodopsin kinase), 37.4% (bovine βARK), 37.2% (bovine βARK2), and 36.5% (Drosophila GPRK-1). PILEUP uses a progressive pairwise alignment.

The overall amino acid sequence of GRK6 was compared with those of other GRKs by construction of a phylogenetic tree (FIG. 8). This comparison suggests that there are two major branches of the GRK family tree. One branch contains bovine βARK, βARK2, and Drosophila GPRK-1 while the other contains bovine rhodopsin kinase, human GRK5, GRK6 and IT11 and Drosophila GPRK-2. GRK6 is most closely related to human GRK5 (70.1% amino acid identity), human IT11 (68.5% identity) and Drosophila GPRK-2 (66.7% identity). The most highly conserved region between these proteins is the protein kinase catalytic domain where GRK6 has 78.7%, 79.5% and 74.9% identity with GRK5, IT11 and GPRK-2, respectively (FIG. 9). The regions of greatest divergence lie in the amino and carboxyl terminal domains. A comparison of the amino terminal domains shows that GRK6 and GRK5 are highly conserved over the first 46 residues (87.0% identity) while over the next 122 amino acids the homology is significantly lower (46.7% identity). By comparison, GRK6 and IT11 are highly conserved over the first 17 amino acids (82.4% identity) but then IT11 has a 32 amino acid gap compared to GRK5, GRK6, βARK, βARK2, GPRK-1 and rhodopsin kinase. Over the next 120 residues, the amino acid identity between GRK6 and IT11 is 46.7%, comparable to that between GRK6 and GRK5. A notable feature of GPRK-2 is that it has a very short N-terminal domain of only 28 amino acids. The C-terminal domains of GRK6, GRK5, IT11 and GPRK-2 are also somewhat conserved with several stretches of very high homology. Overall, the C-terminal domains of GRK6, GRK5, IT11 and GPRK-2 are 145, 159, 100 and 159 amino acids in length, respectively, and share 52–61% amino acid identity. The role of the N- and C-terminal domains of GRK6 have not been established. However, studies using monoclonal antibodies directed against different regions of rhodopsin kinase suggests that the N-terminal region of rhodopsin kinase contains a sequence involved in the recognition of photolyzed rhodopsin. Mutagenesis studies on βARK also suggest that the N-terminal region may play a role in receptor binding. The C-terminal domain of βARK appears to interact with G protein Ad subunits while in rhodopsin kinase the C-terminus is farnesylated. GRK6 contains no consensus sequence for prenylation and it is not activated by G protein PT subunits.

The phylogenetic classification of the GRK family is further supported by functional analyses of the various GRKs. In vitro studies have demonstrated that βARK and βARK2 share a very similar substrate specificity both at the level of amino acid preference (they phosphorylate serine-containing peptides with N-terminal acidic residues), receptor phosphorylation (β$_2$AR, m2 muscarinic cholinergic and substance P are good substrates in vitro), and potential mechanism of cellular activation (interaction with G protein βγ subunits). βARK, βARK2 and Drosophila GPRK-1 also appear to be ubiquitous proteins being expressed in a variety of tissues. In contrast, the specific localization of rhodopsin kinase in rod and cone outer segments suggests that its ability to rapidly phosphorylate light-activated rhodopsin (and possibly the cone opsins) may be its major role. At present, little is known about the function of GRK6, GRK5, IT11 and Drosophila GPRK-2. However, the similarities between these four proteins suggests that they may well share common roles in the cell. As an initial approach to defining the substrate specificity of GRK6, it was expressed in Sf9 insect cells and assessed for activity using rhodopsin as a substrate.

Figure 10A:
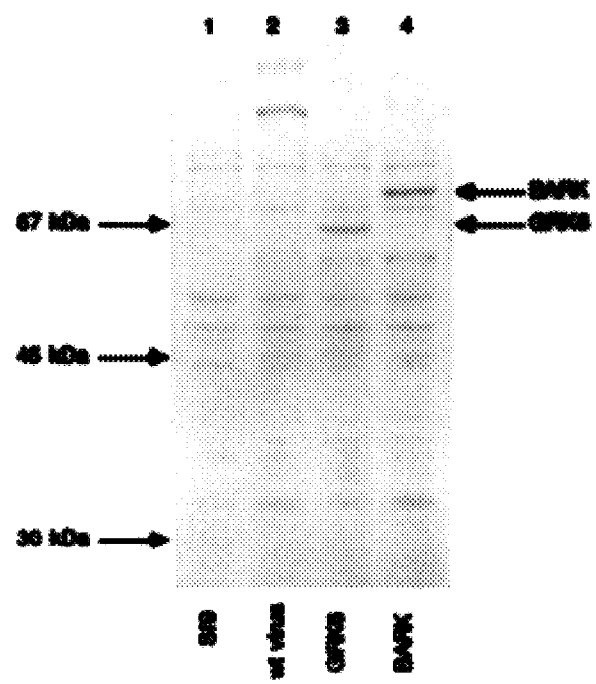
FIG. 10 is the expression of GRK6 in Sf9 Insect Cells. A. GRK6- and βARK-containing baculoviruses were prepared. Sf9 cells, either uninfected (lane 1) or infected with Bac-PAK6 (lane 2) or GRK6-(lane 3) or βARK-(lane 4) containing viruses, were harvested following a 48 hour infection. The cells were lysed, centrifuged and 15 μg of supernatant protein was then electrophoresed on a 10% polyacrylamide gel which was then stained with Coomassie blue. B. The supernatants (5 μg total protein) were also used to phosphorylate urea treated ROS membranes (80 pmol rhodopsin) in the presence (+) or absence (-) of light. Incubations (40 μl total volume) were at 30° C. for 10 minutes and were stopped by the addition of 50 μl of SDS sample buffer. Following polyacrylamide gel electrophoresis, the gels were dried and autoradiographed for 3 hours. From three separate experiments, the GRK6 virus infected supernatant phosphorylated bleached rhodopsin with a specific activity of 81 pmol/min/mg protein (when the BacPAK6 infected cell supernatant phosphorylation of rhodopsin was subtracted). This activity was 4.7%+/–0.4% that of the βARK virus infected supernatant.
Figure 10B:
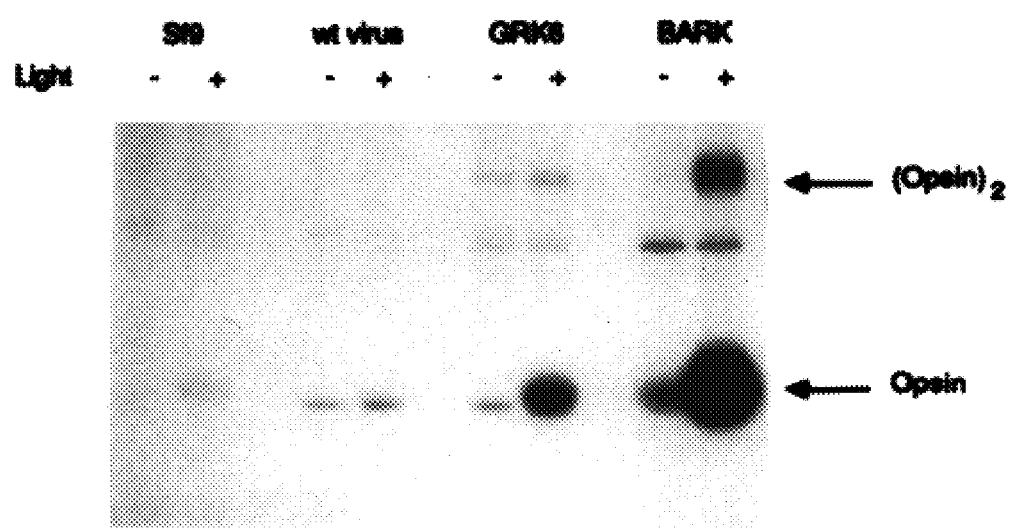

To set up an expression system for GRK6, an ~2 kb ORF NcoI/EcoRI fragment of pGRK6-hb8 was cloned into the baculovirus expression vector pBacPAK1. This construct was co-transfected into Sf9 insect cells with Bsu36I digested BacPAK6 virus to produce a recombinant baculovirus containing the GRK6 cDNA. Sf9 cells were then infected with either the wild type BacPAK6 virus or with the GRK6- or βARK-containing baculovirus. The cells were harvested 48 hours post-infection, homogenized and centrifuged at 40,000×g for 20 minutes. When the supernatant fractions were assessed for protein expression by gel electrophoresis, both GRK6 and βARK were found to be expressed at a high level with GRK6 migrating at ~66 kDa (FIG. 10A, lane 3) and βARK at ~80 kDa (lane 4). The supernatant fractions were then tested for their ability to phosphorylate rhodopsin. Supernatants from both uninfected Sf9 cells and BacPAK6 infected cells phosphorylated rhodopsin to a very low extent (FIG. 10B, lanes 1–4). In contrast, the GRK6-containing cell supernatant was able to phosphorylate rhodopsin in a light dependent fashion (lanes 5 and 6). However, from three separate experiments GRK6 was only 4.7%+/–0.4% as active as βARK (lane 8) when rhodopsin was used as the substrate.

Similar to most other protein kinases, GRK6 displays a preference for $Mg^{2+}$ as the divalent metal cofactor. The optimum concentration was ~2 mM free $Mg^{2+}$ with higher concentrations being inhibitory to the kinase. This concentration is similar to the $Mg^{2+}$ requirements for both βARK and GRK5. The optimum $Mn^{2+}$ concentration was 1 mM which is similar to GRK5. Unlike GRK5, however, 1 mM free $Mn^{2+}$ results in GRK6 activity comparable to that observed for $Mg^{2+}$ while GRK5 displays ~2/3 the activity when $Mn^{2+}$ is present compared to $Mg^{2+}$. Similar experiments with $Ca^{2+}$ or $Zn^{2+}$ as the divalent cofactor show that these ions are incapable of facilitating rhodopsin phosphorylation by GRK6. Furthermore, both $Ca^{2+}$ and $Zn^{2+}$ inhibited GRK6 activity in the presence of $Mg^{2+}$. Another difference between GRK6 and GRK5 is found in their Km for ATP. At a rhodopsin concentration of 3 μM, the Km of GRK6 for ATP is 111 μM, whereas GRK5 exhibits a Km of 18 24 μM.

The ability of purified GRK6 to phosphorylate a specific consensus amino acid sequence was analyzed using a variety of synthetic peptide substrates. The peptides, RRREEESGGG (SEQ ID NO: 7), which is a good substrate for βARK, and RRREEESEEE (SEQ ID NO: 8), which is a good substrate for rhodopsin, were poorly phosphorylated by GRK6. These peptides are not phosphorylated by GRK5. Of all the peptides tested, RRRASAAASAA (SEQ ID NO: 9) was found to be the best substrate for GRK6. Interestingly, the same peptide containing a phosphoserine as the first serine is not phosphorylated by GRK6 indicating that GRK6 either prefers the first serine for phosphorylation or that the acidic environment created by the phosphate group prevents the kinase from phosphorylating the second serine residue. GRK6 activity was also apparent with the RRRAEASAA (SEQ ID NO: 10) peptide but not with the RRRAAAEASAAA (SEQ ID NO: 11) peptide indicating that the basic arginine residues enable GRK6 to phosphorylate the peptide if they are relatively close to the serine residue in a situation where an acidic amino acid is also present. However, kemptide (LRRASLG (SEQ ID NO: 12)), a basic peptide substrate for the cAMP-dependent protein kinase, was a poor substrate for GRK6. Overall, the pattern of peptide phosphorylation is similar to that of GRK5; however, GRK6 activity is ~2–5 fold lower than values for GRK5. From these studies it is apparent that in contrast to βARK and rhodopsin, GRK6, like GRK5, does not phosphorylate serine residues in an acidic environment.

To further characterize GRK6 substrate specificity, several general protein kinase substrates such as histones, casein and phosvitin were studied. As with GRK5, GRK6 was able to phosphorylate the acidic proteins casein and phosvitin while it was only weakly reactive toward the basic protein substrate histones. In experiments with the polyanions, heparin and dextran sulfate, it was demonstrated that GRK6 activity, like GRK5 activity, was strongly inhibited with $IC_{50}$ values of ~15 and 7 nM, respectively. Polyglutamic acid and polyaspartic acid were also tested on GRK6 and found to be relatively strong inhibitors of kinase activity ($IC_{50}$ values of 400 and 487 nM, respectively), but were ~16- and ~6-fold less effective, respectively, as inhibitors compared to GRK5. The compounds H-7 and NaCl were shown to inhibit GRK6 at similar concentrations to that of GRK5.

The ability of polyanions to activate GRK6 was also examined. Spermidine enhanced GRK6 activity -1.4-fold over an optimal concentration range of 0.1 to 0.5 mM, while spermine elevated GRK6 phosphorylation of rhodopsin ~1.5-fold over an optimal concentration range of 0.01 to 0.1 mM. Polylysine was found to the most potent enhancer of GRK6 activity with an ~2.7-fold increase in phosphorylation (optimal range 1 to 10 μM). This overall pattern of polycation activation for GRK6 was similar to GRK5. In addition, low concentrations of various polycations were effective at reversing heparin inhibition of GRK6 while higher concentration activated GRK6.

In contrast to GRK5, however, GRK6 has been found to have a substantially lower ability to autophosphorylate, even in the presence of phospholipid, with a maximal stoichiometry of 0.2 to 0.3 mol of Pi/mol of GRK6. Experiments with several different sources of phospholipid showed no significant increased ability to promote GRK6 autophosphorylation compared to phosphatidylcholine. Thus, it appears that GRK6 uses a different strategy than other G protein-coupled receptor kinases such as GRK5, βARK and rhodopsin kinase for kinase targeting to the plasma membrane and activation.

Figure 11A:
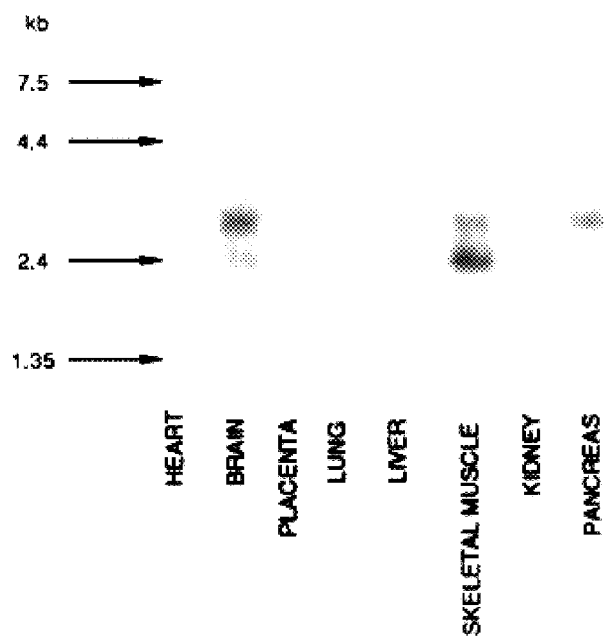
FIG. 11 shows Northern blot analysis of human mRNA from various tissues. A. 2 μg of poly A$^+$ RNA from human heart, brain, placenta, lung, liver, skeletal muscle, kidney and pancreas, was used for RNA analysis. The blot was hybridized with a randomly primed 1780 bp EcoRI fragment from the clone pGRK6-hh2. The blot was washed in 0.1× SSC at 60° C. before autoradiography at –80° C. for 3 days. B. The blot was stripped and then reprobed with a ~1556 bp EcoRI/NcoI ORF fragment from the human βARK cDNA. The blot was again washed in 0.1×SSC at 60° C. before autoradiography at –80° C. for 3 days.
Figure 11B:
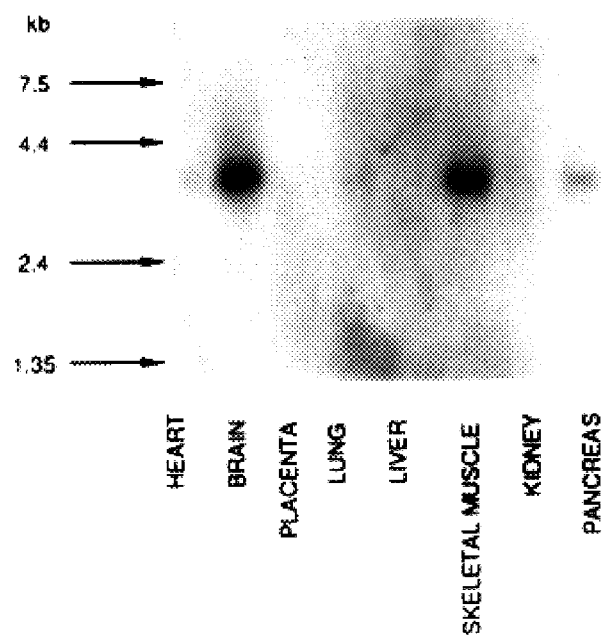

To assess the tissue distribution of GRK6, RNA blot analysis was performed with a 1780 bp ORF fragment from pGRK6-hh2. This fragment was labeled by random priming and used to probe poly $A^+$ selected RNA from 8 human tissues. Two major RNA species of ~3 and ~2.4 kb were observed (was FIG. 11A). The larger message was found at comparable levels in brain, skeletal muscle and pancreas with significantly lower levels being observed in lung, placenta, heart and kidney. In contrast, the smaller message was found predominantly in skeletal muscle with lower levels in brain and still lower levels in pancreas. The significance of the two distinct messages between tissues (e.g., pancreas has predominantly the 3 kb message while skeletal muscle has predominantly the 2.4 kb message) is not known. When the RNA blot was stripped and reprobed with a human βARK cDNA probe, a distinct ~3.8 kb message was seen (was FIG. 11B), similar to that previously observed for bovine βARK. The tissue distribution of human GRK6 and βARK appear to be very similar, with the highest levels for both in brain, skeletal muscle and pancreas and the lowest levels in liver.

GRK5 and GRK6

Thus, two new members of the G protein-coupled receptor kinase family have been identified. In vertebrates, this family presently consists of βARK, 6ARK2, rhodopsin kinase, IT11, and the newly isolated GRK5 and GRK6. Two Drosophila kinases termed GPRK-1 and GPRK-2 have also been identified. Among all the GRKs, rhodopsin kinase appears to be the most appropriately named, given its selected tissue distribution and ability to specifically phosphorylate photolyzed rhodopsin. Since rhodopsin kinase was the first identified G protein-coupled receptor kinase it might well also be termed GRK1. By comparison, βARK appears to play a major role in the phosphorylation and desensitization of the agonist-activated $β_2$-adrenergic receptor, although it is a ubiquitous protein whose expression does not correlate with any particular receptor. In fact, in vitro studies have demonstrated that βARK can phosphorylate numerous receptors including the β2-adrenergic, $α_2$-adrenergic, m2 muscarinic cholinergic and substance P receptors. Thus, βARK may well be more appropriately named GRK2, since it was the second member of this family to be identified. The third member of this family, βARK2 could be termed GRK3, while IT11 could be appropriately represented as GRK4. In this convention the cloning of GRK5 and GRK6, the fifth and sixth members of the GRK family are described.

At present, nothing is known about the substrate specificity of the Drosophila GPRK-2 or the recently identified human GRK, IT11. However, GRK5 has been demonstrated to phosphorylate several G protein-coupled receptors in a stimulus-dependent manner. GRK6 is also able to phosphorylate rhodopsin, $β_2$-adrenergic and m2 muscarinic cholinergic receptors in a stimulus dependent manner, albeit to a significantly lower extent than βARK and GRK5. However, the initial differences between 8ARK, GRK5 and GRK6 in phosphorylating rhodopsin, as well as their distinct tissue distributions, is indicative of their distinct substrate specificities. The involvement of specific GRKs in stimulus dependent protein phosphorylation is believed to serve as a general mechanism for regulating many G protein-coupled receptors.

The GRK5 and GRK6 cDNAs have been expressed, purified and further characterized with regard to their substrate specificity. The availability of these cDNAs enables the generation of reagents to block the activity of endogenous kinases. These include dominant negative mutations which involves mutating a critical lysine residue in the kinase to arginine. This results in a protein kinase which can still bind to its receptor substrate but can no longer transfer a phosphate group to the receptor. Thus, the mutant kinase can block the ability of the endogenous kinase to phosphorylate a given receptor and thereby block desensitization. An alternative strategy for blocking the activity of the endogenous kinase involves the use of antisense oligonucleotides or stably transfected antisense constructs to block expression of the kinase. This will generate a cell with a reduced ability to desensitize to various agents. The ability of the reagent to inhibit the receptor kinase activity, and therefore block agonist-specific desensitization, is then determined by assaying for the ability of the kinase to phosphorylate the receptor for which it is specific. Assays for phosphorylation are well known in the art.

Expression of GRK5 and GRK6 also allows screening for specific inhibitors of these two kinases. For example, it has been demonstrated that both heparin and dextran sulfate are potent inhibitors of GRK5 and GRK6, while these polyanions are relatively weak inhibitors of βARK. Thus, using well known screening techniques, specific inhibitors of individual G-protein coupled kinases can be identified and then utilized to specifically block the activity of a selected G protein-coupled receptor kinase, thus inhibiting receptor desensitization. Specific inhibitors of these kinases may be used therapeutically to either directly modulate the activity of a given receptor (by blocking endogenous desensitization of that receptor) or by augmenting the ability of a given therapeutic agent to stimulate a given receptor (again by blocking desensitization). Expression of GRK5 and GRK6 also allows for screening of specific activators of these two kinases. For example, the polycations, spermidine, spermine and polylysine have been identified as activators of these two kinases. In similar fashion, additional activators can be identified and then utilized to specifically stimulate the activity of GRK5 or GRK6, thus enhancing receptor desensitization. Specific activators of these kinases may be used therapeutically to modulate the activity of an overactive (e.g., oncogenic) receptor (by stimulating the endogenous desensitization of that receptor)

The invention is further illustrated by the following on-limiting examples.

EXAMPLES

Materials

A human Multiple Tissue Northern (MTN) blot and the BacPAK baculovirus expression system were purchased from Clontech. Wildtype *Spodoptera frugiperda* (Sf9) cells were obtained from American Type Culture Collection. Human heart and brain cDNA libraries were obtained from Stratagene. Tissue culture reagents were purchased form Gibco and Sigma while frozen bovine retinas were from George A. Hormel and Co. Taq polymerase was purchased from Promega. Restriction endonuclease and other molecular biology reagents were from Boehringer Mannheim. $[α-^{32}P]dCTP$, $[α-^{35}S]DATP$, and $[γ-^{32}P]ATP$ were purchased from NEN.

Example 1
Polymerase Chain Reaction (GRK5)

Polymerase chain reactions (PCR) initially contained 200 ng DNA template (human heart cDNA), 100 pmol oligonucleotide primers, 50 mM KCl, 10 mM Tris-HCl, pH 8.4, 1.5 mM $MgCl_2$ in a total reaction volume of 25 μl. The samples were heated to 99° C. for 5 minutes, cooled on ice for 3 minutes and then heated to 72° C. followed by the addition of 200 μM dNTPs and 2 units Taq polymerase. The samples were then denatured at 95° C. for one minute, annealed at 40° C. for one minute and extended at 72° C. for three minutes for 5 cycles. This was followed by 30 cycles of denaturation at 95° C. for one minute, annealing at 50° C. for one minute and extension at 72° C. for three minutes. The sense PCR primer used was 5'-ACIGGIAARATGTAYGC-3 (SEQ ID NO: 3) encoding the amino acid sequence T (G/L) KMYA while the antisense PCR primer was 5'-YTCIGGIGCCATRWAIC-3' (SEQ ID NO: 4) encoding G(Y/F)MAPE (I=inosine, R=A+G, Y=T+C, W=T+A). The sense primer also contained an EcoRI restriction site at the 5' end while the antisense primer contained a HindIII restriction site at the 5' end. This facilitated the cloning of the PCR products into EcoRI/HindIII digested pBluescript for further analysis.

Example 2
Isolation of a Full Length cDNA Clone for GRK5

In order to isolate a full length cDNA, the 450 bp PCR product was labeled with $[^{32}P]dCTP$ by random priming and then used to probe a human heart cDNA library in λZAP. The cDNA library was plated at a density of 50,000 pfu/150 mm dish ($10^6$ total clones), transferred to nitrocellulose filters and hybridized with the labeled PCR probe for 48 hours at 37° C. in buffer containing 25-formamide, 5×saline sodium citrate (SSC), 5×Denhardt's solution, 1% SDS, 0.1% sodium pyrophosphate and 100 μg/ml denatured salmon sperm DNA. The filters were initially washed in 2×SSC, 0.1% SDS at 50° C. for 1 hour followed by a high stringency wash in 0.1×SSC, 0.1% SDS at 65° C. for 1 hour. The six clones identified by this procedure were isolated by repeated plating and screening with the labelled PCR product. The isolated clones were then rescued with a helper phage to yield the cDNAs as inserts in pBluescript SK. All six clones were restriction mapped and sequenced by the dideoxy-nucleotide chain termination technique using T3 and T7 primers and oligonucleotide primers synthesized to known regions of the sequence.

Example 3
Northern Blot Analysis (GRK5)

Tissue distribution of the mRNA for GRK5 was analyzed on a human Multiple Tissue Northern (MTN) blot containing 2 μg of poly A⁺ RNA from human heart, brain, placenta, lung, liver, skeletal muscle, kidney and pancreas. A 1157 bp PstI ORF fragment (bp 383–1540) from pGRK5 was isolated and labeled with [$^{32}$p]dCTP by random priming to a specific activity of $3.5 \times 10^9$ cpm/μg. This probe was hybridized with the human MTN blot for 24 hours at 42° C. in a buffer containing 5×SSPE, 10×Denhardt's solution, 100 μg/ml salmon sperm DNA, 50% formamide and 2% SDS. The blot was washed with 2×SSC, 0.1% SDS at room temperature for 1 hour followed by a high stringency wash with 0.1×SSC, 0.1% SDS at 65° C. for 1 hour. The blot was then autoradiographed at −80° C. for 24 hours.

Example 4
Expression of GRK5 Using the Baculovirus System

The GRK5 ORF was initially excised by restriction digestion of the full length clone pGRK5 using NaeI and SmaI. The resulting 1906 bp fragment, including 27 bp of 5' untranslated and 109 bp of 3' untranslated sequence flanking the 1770 bp ORF, was isolated on a 0.8% low melting agarose gel. The baculovirus expression vector pBacPAK1 was digested with BamHI, blunted with Klenow and dephosphorylated with calf intestinal phosphatase. The 1837 bp GRK5 ORF fragment was then ligated into the blunted BamHI site of pBacPAK1 to generate the construct pBacPAK-GRK5.

Monolayers of Sf9 cells (3×106 cells) were co-transfected with 1 μg of the pBacPAK-GRK5 construct and 0.25 μg of Bsu36I digested BacPAK6 viral DNA using the calcium phosphate precipitation technique. The cells were incubated for 4 hours at 27° C. and the medium was then replaced with complete media (TNM-FH, 10% fetal bovine serum, 2.5 μg/ml fungizone, 50 μg/ml streptomycin, 50 μg/ml penicillin). The cells were incubated for 6 days at 27° C. To obtain the isolated recombinant virus, $4 \times 10^6$ cells were plated on a 35 mm dish and the cells were overlaid with 1.5 ml of the diluted viral stock from the transfection. After 1.5 hours, the virus was removed and the cells were overlaid with 5 ml of 1% low melting agarose in complete media. The plates were incubated at 27° C. and isolated plaques were observed after 4–6 days. In order to confirm the presence of the GRK5 cDNA in the recombinant virus, six isolated viruses were amplified and the viral DNA was extracted and analyzed by restriction digestion and Southern blot hybridization. One of these recombinant viruses was chosen for further amplification and characterization of the expressed kinase.

For the purpose of preliminary characterization of GRK5 and to compare it with βARK, the respective recombinant baculoviruses were used to infect a monolayer of Sf9 cells in a 100 mm dish. Following a 48 hour infection, the cells were rinsed with phosphate buffered saline and were harvested by scrapping and homogenizing in 1.5 ml of ice cold buffer containing 20 mM Hepes, pH 7.2, 10 mM EDTA, 0.5 mM -phenylmethylsulfonyl fluoride, 20 μg/ml leupeptin, 200 μg/ml benzamidine, 250 mM NaCl, 0.02% Triton X-100. The cells were lysed with a Brinkman tissue disrupter (30 seconds at 30,000 rpm) and were centrifuged at 40,000×g for 20 minutes. The supernatants were then assessed for the ability to phosphorylate urea treated rod outer segments.

Example 5
Preparation of G Protein βγ Subunits

The GTP binding proteins $G_o$ and $G_i$ were purified from bovine brain by successive chromatography on DEAE Sephacel, Sephacryl S200 and heptylamine-Sepharose. The G protein preparation, consisting primarily of $G_i$ and $G_o$ was further purified by chromatography on a Mono Q column and then stored in 20 mM Tris-HCl, pH 8.0, 1 mM EDTA, 1 mM dithiothreitol, 250 mM NaCl, and 0.05% Lubrol (buffer A) at −80° C. The βγ subunits were isolated by chromatography of the purified G proteins on heptylamine-Sepharose in the presence of AMF (30 μM AlCl3, 6 mM MgCl₂, 10 mM NaF). The AMF and cholate were removed from the βγ subunit preparation by anion exchange chromatography on a Mono Q column. The purified PT subunits were stored in buffer A at −80° C.

Example 6
Receptor Phosphorylation

Rod outer segments (ROS) were prepared in accordance with methods known to those skilled in the art. Rhodopsin kinase free membranes were prepared by suspending the ROS in 50 mM Tris-HCl, pH 8.0, 5 mM EDTA, 5M urea and sonicating. The urea treated ROS were washed several times by centrifugation and resuspended in 50 mM Tris-HCl, pH 7.5 at a protein concentration of ~1 mg/ml. Phosphorylation reactions contained 5 μg of total protein from the Sf9 cell supernatants expressing either GRK5 or βARK, urea treated ROS (80 pmol rhodopsin), 20 mM Tris-HCl, pH 7.5, 2 mM EDTA, 6 mM MgCl₂ and 0.1 mM [γ-$^{32}$P]ATP, in a total reaction volume of 30 μl. When the effect of G protein βγ subunits was assessed, the reactions also contained 0.25 mM dithiothreitol, 0.01% Lubrol and 62 mM NaCl with or without 100 nM βγ subunits. Reactions were incubated at 30° C. for 15 minutes and then stopped by the addition of 50 Al of SDS sample buffer. Samples were electrophoresed on a 10% homogeneous SDS polyacrylamide gel by the method of Laemmli which is well known to those skilled in the art. Gels were dried and autoradiographed at room temperature for 30–120 minutes. The rhodopsin bands in the gel were then cut and counted in a scintillation counter.

Example 7
Isolation and Sequencing of a βARK-Related cDNA

A randomly-primed human heart cDNA library ($10^6$ clones) in λZAP was initially screened with catalytic domain fragments from the clones pβ-ARK3A encoding bovine βARK and pβARK2-1B encoding bovine βARK2. The probes were made by labeling a 717 bp SacI fragment from pβ-ARK3A (bp 630–1347) and a 1210 bp HindIII fragment from pβARK2-1B (bp 328 to 1537) by random priming using [$^{32}$P] dCTP. The cDNA library was plated at a density of ~50,000 plaques/150 mm plate and the DNA was then transferred to nitrocellulose filters using standard procedures. The filters were pre-hybridized for 4 hours at 37° C. in a buffer containing 25% formamide, 5×SSC (1×=150 mM sodium chloride, 15 mM sodium citrate, pH 7.0), 5×Denhardt's solution, 1% sodium dodecyl sulfate (SDS), 0.1% sodium pyrophosphate and 100 μg/ml denatured salmon sperm DNA and then hybridized with the labeled βARK cDNA fragments for 48 hours at 37° C. in the same buffer. The filters were initially washed in 2×SSC, 0.1% SDS buffer at 50° C. and the stringency was then increased by increasing the washing temperature to 60° C. and successively lowering the salt concentration to 0.5×, 0.2× and 0.1×SSC. This procedure identified one clone which hybridized at low but not high stringency (washed off between 0.5× and 0.2×). A number of other clones which hybridized at high stringency (0.1×SSC at 60° C.) were presumed to be βARK or βARK2 and were not pursued further. The one low stringency clone, termed pGRK6-hh1, was purified by replating and screening with the labeled βARK cDNA fragments. The isolated clone was then rescued with a helper phage to yield the insert in the vector Pbluescript. This clone was restriction mapped and sequenced using the dideoxynucleotide chain termination method. Since pGRK6-hh1 was found to be a partial clone, a ~0.6 kb DraII fragment from this clone was isolated, labeled by random priming and used to rescreen the human heart cDNA library. This rescreening yielded one clone, pGRK6-hh2, which was also excised and sequenced. To isolate additional clones, a 1780 bp EcoRI fragment from pGRK6-hh2 was labeled and used to screen a human fetal brain cDNA library. This screening yielded a total of 13 clones which hybridized at high stringency with the pGRK6-hh2 probe. All of these clones were restriction mapped and sequenced with T3, T7 and selected oligonucleotides from the pGRK6-hh2 sequence.

Example 8
Northern Blot Analysis for GRK6

A human multiple tissue Northern (MTN) blot, containing 2 μg of poly A$^+$ RNA from human heart, brain, placenta, lung, liver, skeletal muscle, kidney and pancreas, was used for RNA analysis. The blot was initially hybridized with a randomly primed 1780 bp EcoRI fragment from pGRK6-hh2 in 5×SSPE (1×=150 mM NaCl, 10 mM NaHPO$_4$, 1 mM EDTA, pH 7.0), 50% formamide, 10×Denhardt's solution, 2% SDS and 100 μg/ml denatured salmon sperm DNA. The blot was washed in 0.1×SSC at 60° C. before autoradiography at –80° C. for 3 days. The blot was stripped by boiling in water for 10 minutes and then reprobed with a 1556 bp EcoRI/NcoI ORF fragment (bp 357–1912) from the human βARK cDNA. The blot was again washed in 0.1×SSC at 60° C. before autoradiography at –80° C. for 3 days.

Example 9
Expression of GRK6 Using the Baculovirus System

The clone pGRK6-hb8 (which contains bp 27 to 2064 of the sequence shown in FIG. 7) was used to express GRK6. An ORF fragment of the GRK6 cDNA was prepared by initially linearizing pGRK6-hb8 for 15 minutes with the restriction enzyme NcoI (sites at bp 61 and 748). The linearized DNA was resolved on a 0.8% low melting agarose gel, extracted and then digested with EcoRI (sites at 5' and 3' ends of the cDNA. The reaction was quenched by incubation at 80° C. for 10 minutes and the DNA was then blunted with Klenow in the presence of dNTPs. The resulting 2004 bp insert (cut at bp 61 and 2064) was separated from the vector and shorter inserts by electrophoresis on a 0.8% low melting agarose gel. This insert contains 2 bp of 5' and 274 bp of 3' untranslated sequence surrounding the 1728 bp open reading frame of GRK6 (bp 63–1790). This insert was then ligated into the baculovirus expression vector pBacPAK1 (prepared by cutting with BamHI, blunting with Klenow, and treating with calf intestinal phosphatase).

Sf9 cells were cultured on a monolayer or in suspension (spinner flask, 70 rpm) using TNM-FH medium containing 10% fetal bovine serum and antibiotics (2.5 μg/ml fungizone, 50 μg/ml streptomycin, 50 μg/ml penicillin). To produce a recombinant baculovirus containing the GRK6 cDNA, Sf9 cells were cotransfected with 1 μg of the pBacPAK-GRK6 DNA and 0.25 μg of Bsu36I digested BacPAK6 viral DNA using the calcium phosphate precipitation technique which is well known in the art. The transfected cells were allowed to recover and produce phage particles in culture media for five days and the virus laden media was then used to infect a fresh monolayer of Sf9 cells. The infected cells were overlaid with 1% low melting agarose in complete media and after a 4 day incubation isolated viral plaques were selected. The plaques were eluted into complete media and were amplified by reinfection of a fresh monolayer of Sf9 cells. Using this procedure, it was found that greater than 90% of the viral plaques contained isolated recombinant viruses. The presence of the full length GRK6 cDNA within the genome of the recombinant baculovirus was confirmed by restriction mapping and Southern blotting.

To initially characterize the activity of GRK6 and compare it with that of βARK, the respective recombinant baculoviruses were used to infect a monolayer of Sf9 cells (100 mm dish). Uninfected Sf9 cells and cells infected with the wild type BacPAK6 virus served as controls. The cells were harvested 48 hours post-infection by rinsing the dishes several times with phosphate buffered saline and then scraping and homogenizing the cells in 1.5 ml of ice cold buffer (20 mM Hepes, pH 7.2, 10 mM EDTA, 0.5 mM phenylmethylsulfonyl fluoride, 20 tg/ml leupeptin, 200 μg/ml benzamidine, 0.02% Triton X-100, 250 mM NaCl, 1 mM dithiothreitol). The cells were lysed with a Brinkman tissue disrupter (30 seconds at 30,000 rpm) and centrifuged at 40,000×g for 20 minutes. The supernatants were then assessed for the ability to phosphorylate urea treated rod outer segment membranes.

Example 10
Preparation of Urea-Treated Rod Outer Segments

Rod outer segments (ROS) were prepared. Rhodopsin kinase free membranes were prepared by suspending the ROS in 50 mM Tris-HCl, pH 8.0, 5 mM EDTA, 5.0 M urea and sonicating. The urea treated ROS were washed several times by centrifugation and resuspended in 50 mM Tris-HCl, pH 7.5, at a protein concentration of ~1 mg/ml. Urea-treated ROS showed negligible endogenous kinase activity and consisted of ~90% rhodopsin as assessed by Coomassie blue staining of polyacrylamide gels.

Example 11
Phosphorylation of Rhodopsin

Phosphorylation reactions contained, in total volume of 40 μl, 5 μg of protein from the respective uninfected or GRK6, βARK or BacPAK6 infected Sf9 cell supernatants and urea treated ROS (80 pmol rhodopsin) in 20 mM Tris-HCl, pH 7.5, 2 mM EDTA, 6 mM MgCl$_2$ and 0.10 mM [γ-$^{32}$P]ATP (1 cpm/mol). Incubations were at 30° C. for 10 minutes either in room light or in the dark and were stopped by the addition of 50 μl of SDS sample buffer (8% SDS, 25 mM Tris-HCl, pH 6.5, 10% glycerol, 5% mercaptoethanol and 0.003% bromophenol blue). The samples were electrophoresed on 10% homogenous polyacrylamide slab gels. Following autoradiography, the [$^{32}$P] -labeled rhodopsin bands were excised and counted to determine the pmol of phosphate transferred.

SEQUENCE LISTING (1) GENERAL INFORMATION:

(iii) NUMBER OF SEQUENCES: 12

(2) INFORMATION FOR SEQ ID NO: 1:

(i) SEQUENCE CHARACTERISTICS:
      (A) LENGTH: 2557
      (B) TYPE: NUCLEIC ACID
      (C) STRANDEDNESS: SINGLE
      (D) TOPOLOGY: LINEAR (iv) ANTI-SENSE: NO (xi) SEQUENCE DESCRIPTION: SEQ ID NO: 1:

```
CAGAGGGAGG AAGAAGCGGC GGCGCGGCGG CGGCGGCTCC TCTTTGCAGA                          50

GGGGGAAACT CTTGGGCTGA GAGCAGGAAC AACGCGGTAG GCAAGGCGGG                         100

CTGCTGGCTC CCCCGGCTCC GGCAGCAGCG GCGGCAGCCC GAGCAGCGGC                         150

AGCAGCAGCG GCAGCACCCC AGGCGCTGAC AGCCCCGCCG GCCGGCTCCG                         200

TTGCTGACCG CCGACTGTCA    ATG GAG CTG GAA AAC ATC GTG GCC                      244
                        Met Glu Leu Glu Asn Ile Val Ala
                          1               5

AAC ACG GTC TTG CTG AAA GCC AGG GAA GGG GGC GGA GGA AAG                       286
Asn Thr Val Leu Leu Lys Ala Arg Glu Gly Gly Gly Gly Lys
     10              15                  20

CGC AAA GGG AAA AGC AAG AAG TGG AAA GAA ATC CTG AAG TTC                       328
Arg Lys Gly Lys Ser Lys Lys Trp Lys Glu Ile Leu Lys Phe
         25                  30                  35

CCT CAC ATT AGC CAG TGT GAA GAC CTC CGA AGG ACC ATA GAC                       370
Pro His Ile Ser Gln Cys Glu Asp Leu Arg Arg Thr Ile Asp
             40                  45                  50

AGA GAT TAC TGC AGT TTA TGT GAC AAG CAG CCA ATC GGG AGG                       412
Arg Asp Tyr Cys Ser Leu Cys Asp Lys Gln Pro Ile Gly Arg
                 55                  60

CTG CTT TTC CGG CAG TTT TGT GAA ACC AGG CCT GGG CTG GAG                       454
Leu Leu Phe Arg Gln Phe Cys Glu Thr Arg Pro Gly Leu Glu
 65                  70                  75

TGT TAC ATT CAG TTC CTG GAC TCC GTG GCA GAA TAT GAA GTT                       496
Cys Tyr Ile Gln Phe Leu Asp Ser Val Ala Glu Tyr Glu Val
     80                  85                  90

ACT CCA GAT GAA AAA CTG GGA GAG AAA GGG AAG GAA ATT ATG                       538
Thr Pro Asp Glu Lys Leu Gly Glu Lys Gly Lys Glu Ile Met
         95                 100                 105

ACC AAG TAC CTC ACC CCA AAG TCC CCT GTT TTC ATA GCC CAA                       580
Thr Lys Tyr Leu Thr Pro Lys Ser Pro Val Phe Ile Ala Gln
             110                 115                 120

GTT GGC CAA GAC CTG GTC TCC CAG ACG GAG GAG AAG CTC CTA                       622
Val Gly Gln Asp Leu Val Ser Gln Thr Glu Glu Lys Leu Leu
                 125                 130

CAG AAG CCG TGC AAA GAA CTC TTT TCT GCC TGT GCA CAG TCT                       664
Gln Lys Pro Cys Lys Glu Leu Phe Ser Ala Cys Ala Gln Ser
135                 140                 145

GTC CAC GAG TAC CTG AGG GGA GAA CCA TTC CAC GAA TAT CTG                       706
Val His Glu Tyr Leu Arg Gly Glu Pro Phe His Glu Tyr Leu
     150                 155                 160

GAC AGC ATG TTT TTT GCA CGC TTT CTC CAG TGG AAG TGG TTG                       748
Asp Ser Met Phe Phe Asp Arg Phe Leu Gln Trp Lys Trp Leu
         165                 170                 175
```

```
GAA AGG CAA CCG GTG ACC AAA AAC ACT TTC AGG CAG TAT CGA         790
Glu Arg Gln Pro Val Thr Lys Asn Thr Phe Arg Gln Tyr Arg
            180                 185                 190

GTG CTA GGA AAA GGG GGC TTC GGG GAG GTC TGT GCC TGC CAG         832
Val Leu Gly Lys Gly Gly Phe Gly Glu Val Cys Ala Cys Gln
                195                 200

GTT CGG GCC ACG GGT AAA ATG TAT GCC TGC AAG CGC TTG GAG         874
Val Arg Ala Thr Gly Lys Met Tyr Ala Cys Lys Arg Leu Glu
205                 210                 215

AAG AAG AGG ATC AAA AAG AGG AAA GGG GAG TCC ATG GCC CTC         916
Lys Lys Arg Ile Lys Lys Arg Lys Gly Glu Ser Met Ala Leu
    220                 225                 230

AAT GAG AAG CAG ATC CTC GAG AAG GTC AAC AGT CAG TTT GTG         958
Asn Glu Lys Gln Ile Leu Glu Lys Val Asn Ser Gln Phe Val
        235                 240                 245

GTC AAC CTG GCC TAT GCC TAC GAG ACC AAC GAT GCA CTG TGC        1000
Val Asn Leu Ala Tyr Ala Tyr Glu Thr Lys Asp Ala Leu Cys
            250                 255                 260

TTG GTC CTG ACC ATC ATG AAT GGG GGT GAC GTG AAG TTC CAC        1042
Leu Val Leu Thr Ile Met Asn Gly Gly Asp Leu Lys Phe His
                265                 270

ATC TAC AAC ATG GGC AAC CCT GGC TTC GAG GAG GAG CGG GCC        1084
Ile Tyr Asn Met Gly Asn Pro Gly Phe Glu Glu Glu Arg Ala
275                 280                 285

TTG TTT TAT GCG GCA GAG ATC CTC TGC GGC TTA GAA GAC CTC        1126
Leu Phe Tyr Ala Ala Glu Ile Leu Cys Gly Leu Glu Asp Leu
    290                 295                 300

CAC CGT GAG AAC ACC GTC TAC CGA GAT CTG AAA CCT GAA AAC        1168
His Arg Glu Asn Thr Val Tyr Arg Asp Leu Lys Pro Glu Asn
        305                 310                 315

ATC CTG TTA GAT GAT TAT GGC CAC ATT AGG ATC TCA GAC CTG        1210
Ile Leu Leu Asp Asp Tyr Gly His Ile Arg Ile Ser Asp Leu
            320                 325                 330

GGC TTG GCT GTG AAG ATC CCC GAG GGA GAC CTG ATC CGC GGC        1252
Gly Leu Ala Val Lys Ile Pro Glu Gly Asp Leu Ile Arg Gly
                335                 340

CGG GTG GGC ACT GTT GGC TAC ATG GCC CCC GAA GTC CTG AAC        1294
Arg Val Gly Thr Val Gly Tyr Met Ala Pro Glu Val Leu Asn
345                 350                 355

AAC CAG AGG TAC GGC CTG AGC CCC GAC TAC TGG GGC CTT GGC        1336
Asn Gln Arg Tyr Gly Leu Ser Pro Asp Tyr Trp Gly Leu Gly
    360                 365                 370

TGC CTC ATC TAT GAG ATG ATC GAG GGC CAG TCG CCG TTC CGC        1378
Cys Leu Ile Tyr Glu Met Ile Glu Gly Gln Ser Pro Phe Arg
        375                 380                 385

GGC CGT AAG GAG AAG GTG AAG CGG GAG GAG GTG GAC CGC CGG        1420
Gly Arg Lys Glu Lys Val Lys Arg Glu Glu Val Asp Arg Arg
            390                 395                 400

GTC CTG GAG ACG GAG GAG GTG TAC TCC CAC AAG TTC TCC GAG        1462
Val Leu Glu Thr Glu Glu Val Tyr Ser His Lys Phe Ser Glu
                405                 410

GAG GCC AAG TCC ATC TGC AAG ATG CTG CTC ACG AAA GAT GCG        1504
Glu Ala Lys Ser Ile Cys Lys Met Leu Leu Thr Lys Asp Ala
415                 420                 425

AAG CAG AGG CTG GGC TGC CAG GAG GAG GGG GCT GCA GAG GTC        1546
Lys Gln Arg Leu Gly Cys Gln Glu Glu Gly Ala Ala Glu Val
    430                 435                 440

AAG AGA CAC CCC TTC TTC AGG AAC ATG AAC TTC AAG CGC TTA        1588
Lys Arg His Pro Phe Phe Arg Asn Met Asn Phe Lys Arg Leu
```

```
                  445                 450                 455
GAA GCC GGG ATG TTG GAC CCT CCC TTC GTT CCA GAC CCC CGC              1630
Glu Ala Gly Met Leu Asp Pro Pro Phe Val Pro Asp Pro Arg
            460                 465                 470

GCT GTG TAC TGT AAG GAC GTG CTG GAC ATC GAG CAG TTC TCC              1672
Ala Val Tyr Cys Lys Asp Val Leu Asp Ile Glu Gln Phe Ser
                475                 480

ACT GTG AAG GGC GTC AAT CTG GAC CAC ACA GAC GAC GAC TTC              1714
Thr Val Lys Gly Val Asn Leu Asp His Thr Asp Asp Asp Phe
485                 490                 495

TAC TCC AAG TTC TCC ACG GGC TCT GTG TCC ATC CCA TGG CAA              1756
Tyr Ser Lys Phe Ser Thr Gly Ser Val Ser Ile Pro Trp Gln
    500                 505                 510

AAC GAG ATG ATA GAA ACA GAA TGC TTT AAG GAG CTG AAC GTG              1798
Asn Glu Met Ile Glu Thr Glu Cys Phe Lys Glu Leu Asn Val
        515                 520                 525

TTT GGA CCT AAT GGT ACC CTC CCG CCA GAT CTG AAC AGA AAC              1840
Phe Gly Pro Asn Gly Thr Leu Pro Pro Asp Leu Asn Arg Asn
            530                 535                 540

CAC CCT CCG GAA CCG CCC AAG AAA GGG CTG CTC CAG AGA CTC              1882
His Pro Pro Glu Pro Pro Lys Lys Gly Leu Leu Gln Arg Leu
                545                 550

TTC AAG CGG CAG CAT CAG AAC AAT TCC AAG AGT TCG CCC AGC              1924
Phe Lys Arg Gln His Gln Asn Asn Ser Lys Ser Ser Pro Ser
555                 560                 565

TCC AAG ACC AGT TTT AAC CAC CAC ATA AAC TCA AAC CAT GTC              1966
Ser Lys Thr Ser Phe Asn His His Ile Asn Ser Asn His Val
    570                 575                 580

AGC TCG AAC TCC ACC GGA AGC AGC TAGTTTCGGC TCTGGCCTCC                2010
Ser Ser Asn Ser Thr Gly Ser Ser
            585                 590

AAGTCCACAG TGGAACCAGC CCAGACCCTT CTCCTTAGAA GTGGAAGTAG               2060

TGGAGCCCCT GCTCTGGTGG GGCTGCCAGG GGAGACCCCG GGAGCCGGAA               2110

GGAGGCCGTC CATCCCGTCG ACGTAGAACC TCGAGGTTTC TCAAAGAAAT               2160

TTCCACTCAG GTCTGTTTTC CGAGGCGGCC CCGGGCGGGT GGATTGGATT               2210

TGTCTTTGGT GAACATTGCA ATAGAAATCC AATTGGATAC GACAACTTGC               2260

ACGTATTTTA ATAGCGTCAT AACTAGAACT GAATTTTGTC TTTATGATTT               2310

TTAAAGAAAA GTTTTGTAAA TTTCTCTACT GTCTCAGTTT ACATTTTCGG               2360

TATATTTGTA TTTAAATGAA GTGAGACTTT GAGGGTGTAT ATTTTCTGTG               2410

CAGCCACTGT TAAGCCATGT GTTCCAAGGC ATTTTAGCGG GGAGGGGGTT               2460

ATCAAAAAAA AAAAAAATGT GACTCAAGAC TTCCAGAGCC TCAAATGAGA               2510

AAATGTCTTT ATTAAATGTA GAAAGTGATC CATACTTCAA AAAAAAA                  2557

(2) INFORMATION FOR SEQ ID NO: 2:

(i) SEQUENCE CHARACTERISTICS:
        (A) LENGTH: 2848
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 2:

CGCGGCACTC GCGCGCGATC CCGGCCGGCG GCGCGCCGGC GGGCCAGGCG               50
```

-continued

```
GCGCCACAGC CC ATG GAG CTC GAG AAC ATC GTA GCG AAC ACG                92
              Met Glu Leu Glu Asn Ile Val Ala Asn Thr
                1               5                  10

GTG CTA CTC AAG GCC CGG GAA GGT GGC GGT GGA AAT CGC AAA GGC          137
Val Leu Leu Lys Ala Arg Glu Gly Gly Gly Gly Asn Arg Lys Gly
                15                  20                  25

AAA AGC AAG AAA TGG CGG CAG ATG CTC CAG TTC CCT CAC ATC AGC          182
Lys Ser Lys Lys Trp Arg Gln Met Leu Gln Phe Pro His Ile Ser
                30                  35                  40

CAG TGC GAA GAG CTG CGG CTC AGC CTC GAG CGT GAC TAT CAC AGC          227
Gln Cys Glu Glu Leu Arg Leu Ser Leu Glu Arg Asp Tyr His Ser
                45                  50                  55

CTG TGC GAG CGG CAC GCC ATT GGG CGC CTG CTG TTC CGA GAG TTC          272
Leu Cys Glu Arg His Ala Ile Gly Arg Leu Leu Phe Arg Glu Phe
                60                  65                  70

TGT GCC ACG AGG CCG GAG CTG AGC CGC TGC GTC GCC TTC CTG GAT          317
Cys Ala Thr Arg Pro Glu Leu Ser Arg Cys Val Ala Phe Leu Asp
                75                  80                  85

GGG GTG GCC GAG TAT GAA GTG ACC CCG GAT GAC AAG CGG AAG GCA          362
Gly Val Ala Glu Tyr Glu Val Thr Pro Asp Asp Lys Arg Lys Ala
                90                  95                 100

TGT GGG CGG CAC GTA ACG CAG AAT TTT CTG AGC CAC ACG GGT CCT          407
Cys Gly Arg His Val Thr Gln Asn Phe Leu Ser His Thr Gly Pro
               105                 110                 115

GAC CTC ATC CCT GAG GTC CCC CGG CAG CTG GTG ACG AAC TGC ACC          452
Asp Leu Ile Pro Glu Val Pro Arg Gln Leu Val Thr Asn Cys Thr
               120                 125                 130

CAG CGG CTG GAG CAG GGT CCC TGC AAA GAC CTT TTC CAG GAA CTC          497
Gln Arg Leu Glu Gln Gly Pro Cys Lys Asp Leu Phe Gln Glu Leu
               135                 140                 145

ACC CGG CTG ACC CAC GAG TAC CTG AGC GTG GCC CCT TTT GCC GAC          542
Thr Arg Leu Thr His Glu Tyr Leu Ser Val Ala Pro Phe Ala Asp
               150                 155                 160

TAC CTC GAC AGC ATC TAC TTC AAC CGT TTC CTG CAG TGG AAG TGG          587
Tyr Leu Asp Ser Ile Tyr Phe Asn Arg Phe Leu Gln Trp Lys Trp
               165                 170                 175

CTG GAA AGG CAG CCA GTG ACC AAA AAC ACC TTC AGG CAA TAC CGA          632
Leu Glu Arg Gln Pro Val Thr Lys Asn Thr Phe Arg Gln Tyr Arg
               180                 185                 190

GTC CTG GGC AAA GGT GGC TTT GGG GAG GTG TGC GCC TGC CAG GTG          677
Val Leu Gly Lys Gly Gly Phe Gly Glu Val Cys Ala Cys Gln Val
               195                 200                 205

CGG GCC ACA GGT AAG ATG TAT GCC TGC AAG AAG CTA GAG AAA AAG          722
Arg Ala Thr Gly Lys Met Tyr Ala Cys Lys Lys Leu Glu Lys Lys
               210                 215                 220

CGG ATC AAG AAG CGG AAA GGG GAG GCC ATG GCG CTG AAC GAG AAG          767
Arg Ile Lys Lys Arg Lys Gly Glu Ala Met Ala Leu Asn Glu Lys
               225                 230                 235

CAG ATC CTG GAG AAA GTG AAC AGT AGG TTT GTA GTG AGC TTG GCC          812
Gln Ile Leu Glu Lys Val Asn Ser Arg Phe Val Val Ser Leu Ala
               240                 245                 250

TAC GCC TAT GAG ACC AAG GAC GCG CTG TGC CTG GTG CTG ACA CTG          857
Tyr Ala Tyr Glu Thr Lys Asp Ala Leu Cys Leu Val Leu Thr Leu
               255                 260                 265

ATG AAC GGG GGC GAC CTC AAG TTC CAC ATC TAC CAC ATG GGC CAG          902
Met Asn Gly Gly Asp Leu Lys Phe His Ile Tyr His Met Gly Gln
               270                 275                 280

GCT GGC TTC CCC GAA GCG CGG GCC GTC TTC TAC GCC GCC GAG ATC          947
Ala Gly Phe Pro Glu Ala Arg Ala Val Phe Tyr Ala Ala Glu Ile
               285                 290                 295
```

```
TGC TGT GGC CTG GAG GAC CTG CAC CGG GAG CGC ATC GTG TAC AGG          992
Cys Cys Gly Leu Glu Asp Leu His Arg Glu Arg Ile Val Tyr Arg
                300                 305                 310

GAC CTG AAG CCC GAG AAC ATC TTG CTG GAT GAC CAC GGC CAC ATC         1037
Asp Leu Lys Pro Glu Asn Ile Leu Leu Asp Asp His Gly His Ile
                315                 320                 325

CGC ATC TCT GAC CTG GGA CTA GCT GTG CAT GTG CCC GAG GGC CAG         1082
Arg Ile Ser Asp Leu Gly Leu Ala Val His Val Pro Glu Gly Gln
                330                 335                 340

ACC ATC AAA GGG CGT GTG GGC ACC GTG GGT TAC ATG GCT CCG GAG         1127
Thr Ile Lys Gly Arg Val Gly Thr Val Gly Tyr Met Ala Pro Glu
                345                 350                 355

GTG GTG AAG AAT GAA CGG TAC ACG TTC AGC CCT GAC TGG TGG GCG         1172
Val Val Lys Asn Glu Arg Tyr Thr Phe Ser Pro Asp Trp Trp Ala
                360                 365                 370

CTC GGC TGC CTC CTG TAC GAG ATG ATC ACA GGC CAG TCG CCC TTC         1217
Leu Gly Cys Leu Leu Tyr Glu Met Ile Ala Gly Gln Ser Pro Phe
                375                 380                 385

CAG CAG AGG AAG AAG AAG ATC AAG CGG GAG GAG GTG GAG CGG CTG         1262
Gln Gln Arg Lys Lys Lys Ile Lys Arg Glu Glu Val Glu Arg Leu
                390                 395                 400

GTG AAG GAG GTC CCC GAG GAG TAT TCC GAG CGG TTT TCC CCG CAG         1307
Val Lys Glu Val Pro Glu Glu Tyr Ser Glu Arg Phe Ser Pro Gln
                405                 410                 415

GCC CGC TCA CTT TGC TCA CAG CTC CTC TGC AAG GAC CCT GCC GAA         1352
Ala Arg Ser Leu Cys Ser Gln Leu Leu Cys Lys Asp Pro Ala Glu
                420                 425                 430

CGC CTG GGG TGT CGT GGG GGC AGT GCC CGC GAG GTG AAG GAG CAC         1397
Arg Leu Gly Cys Arg Gly Gly Ser Ala Arg Glu Val Lys Glu His
                435                 440                 445

CCC CTC TTT AAG AAG CTG AAC TTC AAG CGG CTG GGA GCT GGC ATG         1442
Pro Leu Phe Lys Lys Leu Asn Phe Lys Arg Leu Gly Ala Gly Met
                450                 455                 460

CTG GAG CCG CCG TTC AAG CCT GAC CCC CAG GCC ATT TAC TGC AAG         1487
Leu Glu Pro Pro Phe Lys Pro Asp Pro Gln Ala Ile Tyr Cys Lys
                465                 470                 475

GAT GTT CTG GAC ATT GAA CAG TTC TCT ACG GTC AAG GGC GTG GAG         1532
Asp Val Leu Asp Ile Glu Gln Phe Ser Tyr Val Lys Gly Val Glu
                480                 485                 490

CTG GAG CCT ACC GAC CAG CAG TTC TAC CAG AAG TTT GCC ACA GGC         1577
Leu Glu Pro Thr Asp Gln Gln Phe Tyr Gln Lys Phe Ala Thr Gly
                495                 500                 505

AGT GTG CCC ATC CCC TGG CAG AAC GAG ATG GTG GAG ACC GAG TGC         1622
Ser Val Pro Ile Pro Trp Gln Asn Glu Met Val Glu Thr Glu Cys
                510                 515                 520

TTC CAA GAG CTG AAT GTC TTT GGG CTG GAT GGC TCA GTT CCC CCA         1667
Phe Gln Glu Leu Asn Val Phe Gly Leu Asp Gly Ser Val Pro Pro
                525                 530                 535

GAC CTG GAC TGG AAG GGC CAG CCA CCT GCA CCT CCT AAA AAG GGA         1712
Asp Leu Asp Trp Lys Gly Gln Pro Pro Ala Pro Pro Lys Lys Gly
                540                 545                 550

CTG CTG CAG AGA CTC TTC AGT CGC CAA GAT TGC TGT GGA AAC TGC         1757
Leu Leu Gln Arg Leu Phe Ser Arg Gln Asp Cys Cys Gly Asn Cys
                555                 560                 565

AGC GAC AGC GAG GAA GAG CTC CCC ACC CGC CTC                         1790
Ser Asp Ser Glu Glu Glu Leu Pro Thr Arg Leu
                570                 575

TAGCCCCCAG CCCGAGGCCC CCACCAGCAG TTGGCGGTAG CAGCTACTCC GAGCGCCGTT   1850
```

| | |
|---|---|
| TACAGTTTTG CACAGTGATC TTCCCCATTG TCCACTCAAG TCGTGGCCTG | 1900 |
| GGGAACACAG ACGGAGCTGT CCCCAGTGTC CTCCGTCCCT CAGCCCCTGG | 1950 |
| CCTGGCTGAG TTTGGCAGGG CCTGGGCCAT CCCTGGGACA AAGGTGCGTC | 2000 |
| CCTTCAGCTC TTCTCCGTGG AGCTCGGGGC TTTCTGTATT TATGTATTTG | 2050 |
| TACGAATGTA TATAGCGACC AGAGCATTCT TAATTCCCGC CGCAGACCTG | 2100 |
| GCGCCCCCGC CTTGGCTCCT GGGGCAGCC AGCCCTGGCT GGAGAGCGGG | 2150 |
| ACGTGGCAGA GGAGCCACTG CCAAACTCAA GGCTCCTCTG GCCCAGCTTG | 2200 |
| GATGGCTGAG GGTGGTCACA CCTGAGCCTT CAGCACTGTG CTGCCACCCC | 2250 |
| GGCCTCTGAG TAAGACTCGT GCCTCCCCCT GCTGCCCTGG GCTCAGGCTG | 2300 |
| CTACCTCTGG GGCCCAAAGC TGTCCCTTCT CAGTGCTTGT CAGCGCTGGG | 2350 |
| TCTGGGGCCT CTGTATGCCC TAGGCCTGTG CCAAAGTGGC CAGAGATTGG | 2400 |
| GCTGCCTGTG ATACCCATCA GCCCACTGCC CCGGCCGGCC CAGATAGGTC | 2450 |
| TGCCTCTGCC TTCCAGCTCC CACAGCCTGG TCCCTGATAC TGGGCTCTGT | 2500 |
| CCTGCAGACA CCTCTTTCAG AAACGCCCAA GCCCAGCCCT AGGAGGGGGT | 2550 |
| GGGGCATCCC TGGTCAACCC TCAAACATTC CGGACTCCCC TCATAACAAT | 2600 |
| AGACACATGT GCCCAGCAAT AATCCGCCCC TTCCTGTGTG CGCCTGTGGG | 2650 |
| GTGCGTGCTC TCTGTGTGTA CCTGTGTGGG TGAAGGGGAT AGGGCGAGGC | 2700 |
| TGTGCCTGTG CCCCAGGTCC CAGCCCTGGC CCTTCCCAGA CTGTGATGGC | 2750 |
| CATCCTGGTC CCAGTGTTAG GGTAGCATGG GATTACAGGG CCCTGTTTTT | 2800 |
| TCCATATTTA AAGCCAATTT TTATTACTCG TTTTGTCCAA CGTAAAAG | 2848 |

(2) INFORMATION FOR SEQ ID NO: 3:

(i) SEQUENCE CHARACTERISTICS:
        (A) LENGTH: 17
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 3:

| | |
|---|---|
| ACNGGNAARA TGTAYGC | 17 |

(2) INFORMATION FOR SEQ ID NO: 4:

(i) SEQUENCE CHARACTERISTICS:
        (A) LENGTH: 17
        (B) TYPE: NUCLEIC ACID
        (C) STRANDEDNESS: SINGLE
        (D) TOPOLOGY: LINEAR (iv) ANTI-SENSE: YES (xi) SEQUENCE DESCRIPTION: SEQ ID NO: 4:

| | |
|---|---|
| YTCNGGNGCC ATRWANC | 17 |

(2) INFORMATION FOR SEQ ID NO: 5:

(i) SEQUENCE CHARACTERISTICS:
        (A) LENGTH: 590
        (B) TYPE: AMINO ACID
        (D) TOPOLOGY: LINEAR (xi) SEQUENCE DESCRIPTION: SEQ ID NO: 5:

```
Met Glu Leu Glu Asn Ile Val Ala Asn Thr Val Leu Leu Lys Ala
1               5                   10                  15

Arg Glu Gly Gly Gly Lys Arg Lys Gly Lys Ser Lys Lys Trp
                20                  25                  30

Lys Glu Ile Leu Lys Phe Pro His Ile Ser Gln Cys Glu Asp Leu
                35                  40                  45

Arg Arg Thr Ile Asp Arg Asp Tyr Cys Ser Leu Cys Asp Lys Gln
                50                  55                  60

Pro Ile Gly Arg Leu Leu Phe Arg Gln Phe Cys Glu Thr Arg Pro
                65                  70                  75

Gly Leu Glu Cys Tyr Ile Gln Phe Leu Asp Ser Val Ala Glu Tyr
                80                  85                  90

Glu Val Thr Pro Asp Glu Lys Leu Gly Glu Lys Gly Lys Glu Ile
                95                  100                 105

Met Thr Lys Tyr Leu Thr Pro Lys Ser Pro Val Phe Ile Ala Gln
                110                 115                 120

Val Gly Gln Asp Leu Val Ser Gln Thr Glu Glu Lys Leu Leu Gln
                125                 130                 135

Lys Pro Cys Lys Glu Leu Phe Ser Ala Cys Ala Gln Ser Val His
                140                 145                 150

Glu Tyr Leu Arg Gly Glu Pro Phe His Glu Tyr Leu Asp Ser Met
                155                 160                 165

Phe Phe Asp Arg Phe Leu Gln Trp Lys Trp Leu Glu Arg Gln Pro
                170                 175                 180

Val Thr Lys Asn Thr Phe Arg Gln Tyr Arg Val Leu Gly Lys Gly
                185                 190                 195

Gly Phe Gly Glu Val Cys Ala Cys Gln Val Arg Ala Thr Gly Lys
                200                 205                 210

Met Tyr Ala Cys Lys Arg Leu Glu Lys Lys Arg Ile Lys Lys Arg
                215                 220                 225

Lys Gly Glu Ser Met Ala Leu Asn Glu Lys Gln Ile Leu Glu Lys
                230                 235                 240

Val Asn Ser Gln Phe Val Val Asn Leu Ala Tyr Ala Tyr Glu Thr
                245                 250                 255

Lys Asp Ala Leu Cys Leu Val Leu Thr Ile Met Asn Gly Gly Asp
                260                 265                 270

Leu Lys Phe His Ile Tyr Asn Met Gly Asn Pro Gly Phe Glu Glu
                275                 280                 285

Glu Arg Ala Leu Phe Tyr Ala Ala Glu Ile Leu Cys Gly Leu Glu
                290                 295                 300

Asp Leu His Arg Glu Asn Thr Val Tyr Arg Asp Leu Lys Pro Glu
                305                 310                 315

Asn Ile Leu Leu Asp Asp Tyr Gly His Ile Arg Ile Ser Asp Leu
                320                 325                 330

Gly Leu Ala Val Lys Ile Pro Glu Gly Asp Leu Ile Arg Gly Arg
                335                 340                 345

Val Gly Thr Val Gly Tyr Met Ala Pro Glu Val Leu Asn Asn Gln
                350                 355                 360

Arg Tyr Gly Leu Ser Pro Asp Tyr Trp Gly Leu Gly Cys Leu Ile
                365                 370                 375

Tyr Glu Met Ile Glu Gly Gln Ser Pro Phe Arg Gly Arg Lys Glu
                380                 385                 390
```

```
Lys Val Lys Arg Glu Glu Val Asp Arg Arg Val Leu Glu Thr Glu
            395                 400                 405

Glu Val Tyr Ser His Lys Phe Ser Glu Ala Lys Ser Ile Cys
            410                 415                 420

Lys Met Leu Leu Thr Lys Asp Ala Lys Gln Arg Leu Gly Cys Gln
            425                 430                 435

Glu Glu Gly Ala Ala Glu Val Lys Arg His Pro Phe Phe Arg Asn
            440                 445                 450

Met Asn Phe Lys Arg Leu Glu Ala Gly Met Leu Asp Pro Pro Phe
            455                 460                 465

Val Pro Asp Pro Arg Ala Val Tyr Cys Lys Asp Val Leu Asp Ile
            470                 475                 480

Glu Gln Phe Ser Thr Val Lys Gly Val Asn Leu Asp His Thr Asp
            485                 490                 495

Asp Asp Phe Tyr Ser Lys Phe Ser Thr Gly Ser Val Ser Ile Pro
            500                 505                 510

Trp Gln Asn Glu Met Ile Glu Thr Glu Cys Phe Lys Glu Leu Asn
            515                 520                 525

Val Phe Gly Pro Asn Gly Thr Leu Pro Pro Asp Leu Asn Arg Asn
            530                 535                 540

His Pro Pro Glu Pro Pro Lys Lys Gly Leu Leu Gln Arg Leu Phe
            545                 550                 555

Lys Arg Gln His Gln Asn Asn Ser Lys Ser Ser Pro Ser Ser Lys
            560                 565                 570

Thr Ser Phe Asn His His Ile Asn Ser Asn His Val Ser Ser Asn
            575                 580                 585

Ser Thr Gly Ser Ser
            590

(2) INFORMATION FOR SEQ ID NO: 6:

(i) SEQUENCE CHARACTERISTICS:
        (A) LENGTH: 576
        (B) TYPE: AMINO ACID
        (D) TOPOLOGY: LINEAR (xi) SEQUENCE DESCRIPTION: SEQ ID NO: 6:

Met Glu Leu Glu Asn Ile Val Ala Asn Thr Val Leu Leu Lys Ala
1               5                   10                  15

Arg Glu Gly Gly Gly Asn Arg Lys Gly Lys Ser Lys Lys Trp
                20                  25                  30

Arg Gln Met Leu Gln Phe Pro His Ile Ser Gln Cys Glu Glu Leu
            35                  40                  45

Arg Leu Ser Leu Glu Arg Asp Tyr His Ser Leu Cys Glu Arg His
            50                  55                  60

Ala Ile Gly Arg Leu Leu Phe Arg Glu Phe Cys Ala Thr Arg Pro
            65                  70                  75

Glu Leu Ser Arg Cys Val Ala Phe Leu Asp Gly Val Ala Glu Tyr
            80                  85                  90

Glu Val Thr Pro Asp Asp Lys Arg Lys Ala Cys Gly Arg His Val
            95                  100                 105

Thr Gln Asn Phe Leu Ser His Thr Gly Pro Asp Leu Ile Pro Glu
            110                 115                 120

Val Pro Arg Gln Leu Val Thr Asn Cys Thr Gln Arg Leu Glu Gln
            125                 130                 135
```

-continued

Gly Pro Cys Lys Asp Leu Phe Gln Glu Leu Thr Arg Leu Thr His
               140                 145                 150

Glu Tyr Leu Ser Val Ala Pro Phe Ala Asp Tyr Leu Asp Ser Ile
               155                 160                 165

Tyr Phe Asn Arg Phe Leu Gln Trp Lys Trp Leu Glu Arg Gln Pro
               170                 175                 180

Val Thr Lys Asn Thr Phe Arg Gln Tyr Arg Val Leu Gly Lys Gly
               185                 190                 195

Gly Phe Gly Glu Val Cys Ala Cys Gln Val Arg Ala Thr Gly Lys
               200                 205                 210

Met Tyr Ala Cys Lys Lys Leu Glu Lys Lys Arg Ile Lys Lys Arg
               215                 220                 225

Lys Gly Glu Ala Met Ala Leu Asn Glu Lys Gln Ile Leu Glu Lys
               230                 235                 240

Val Asn Ser Arg Phe Val Val Ser Leu Ala Tyr Ala Tyr Glu Thr
               245                 250                 255

Lys Asp Ala Leu Cys Leu Val Leu Thr Leu Met Asn Gly Gly Asp
               260                 265                 270

Leu Lys Phe His Ile Tyr His Met Gly Gln Ala Gly Phe Pro Glu
               275                 280                 285

Ala Arg Ala Val Phe Tyr Ala Ala Glu Ile Cys Cys Gly Leu Glu
               290                 295                 300

Asp Leu His Arg Glu Arg Ile Val Tyr Arg Asp Leu Lys Pro Glu
               305                 310                 315

Asn Ile Leu Leu Asp Asp His Gly His Ile Arg Ile Ser Asp Leu
               320                 325                 330

Gly Leu Ala Val His Val Pro Glu Gly Gln Thr Ile Lys Gly Arg
               335                 340                 345

Val Gly Thr Val Gly Tyr Met Ala Pro Glu Val Val Lys Asn Glu
               350                 355                 360

Arg Tyr Thr Phe Ser Pro Asp Trp Trp Ala Leu Gly Cys Leu Leu
               365                 370                 375

Tyr Glu Met Ile Ala Gly Gln Ser Pro Phe Gln Gln Arg Lys Lys
               380                 385                 390

Lys Ile Lys Arg Glu Glu Val Glu Arg Leu Val Lys Glu Val Pro
               395                 400                 405

Glu Glu Tyr Ser Glu Arg Phe Ser Pro Gln Ala Arg Ser Leu Cys
               410                 415                 420

Ser Gln Leu Leu Cys Lys Asp Pro Ala Glu Arg Leu Gly Cys Arg
               425                 430                 435

Gly Gly Ser Ala Arg Glu Val Lys Glu His Pro Leu Phe Lys Lys
               440                 445                 450

Leu Asn Phe Lys Arg Leu Gly Ala Gly Met Leu Glu Pro Pro Phe
               455                 460                 465

Lys Pro Asp Pro Gln Ala Ile Tyr Cys Lys Asp Val Leu Asp Ile
               470                 475                 480

Glu Gln Phe Ser Tyr Val Lys Gly Val Glu Leu Glu Pro Thr Asp
               485                 490                 495

Gln Asp Phe Tyr Gln Lys Phe Ala Thr Gly Ser Val Pro Ile Pro
               500                 505                 510

Trp Gln Asn Glu Met Val Glu Thr Glu Cys Phe Gln Glu Leu Asn
               515                 520                 525

Val Phe Gly Leu Asp Gly Ser Val Pro Pro Asp Leu Asp Trp Lys

```
                       530                 535                 540
Gly Gln Pro Pro Ala Pro Pro Lys Lys Gly Leu Leu Gln Arg Leu
                       545                 550                 555
Phe Ser Arg Gln Asp Cys Cys Gly Asn Cys Ser Asp Ser Glu Glu
                       560                 565                 570
Glu Leu Pro Thr Arg Leu
                575
```

(2) INFORMATION FOR SEQ ID NO: 7:

(i) SEQUENCE CHARACTERISTICS:
        (A) LENGTH: 10
        (B) TYPE: Amino Acid
        (D) TOPOLOGY: Linear (xi) SEQUENCE DESCRIPTION: SEQ ID NO: 7:

```
ARG ARG ARG GLU GLU GLU SER GLY GLY GLY
1               5                   10
```

(2) INFORMATION FOR SEQ ID NO: 8:

(i) SEQUENCE CHARACTERISTICS:
        (A) LENGTH: 10
        (B) TYPE: Amino Acid
        (D) TOPOLOGY: Linear (xi) SEQUENCE DESCRIPTION: SEQ ID NO: 8:

```
ARG ARG ARG GLU GLU GLU SER GLU GLU GLU
1               5                   10
```

(2) INFORMATION FOR SEQ ID NO: 9:

(i) SEQUENCE CHARACTERISTICS:
        (A) LENGTH: 11
        (B) TYPE: Amino Acid
        (D) TOPOLOGY: Linear (xi) SEQUENCE DESCRIPTION: SEQ ID NO: 9:

```
ARG ARG ARG ALA SER ALA ALA ALA SER ALA ALA
1               5                   10
```

(2) INFORMATION FOR SEQ ID NO: 10:

(i) SEQUENCE CHARACTERISTICS:
        (A) LENGTH: 9
        (B) TYPE: Amino Acid
        (D) TOPOLOGY: Linear (xi) SEQUENCE DESCRIPTION: SEQ ID NO: 10:

```
ARG ARG ARG ALA GLU ALA SER ALA ALA
1               5
```

(2) INFORMATION FOR SEQ ID NO: 11:

(i) SEQUENCE CHARACTERISTICS:
        (A) LENGTH: 12
        (B) TYPE: Amino Acid
        (D) TOPOLOGY: Linear (xi) SEQUENCE DESCRIPTION: SEQ ID NO: 11:

```
ARG ARG ARG ALA ALA ALA GLU ALA SER ALA ALA ALA
1               5                   10
```

(2) INFORMATION FOR SEQ ID NO: 12:

```
    (i) SEQUENCE CHARACTERISTICS:
        (A) LENGTH: 7
        (B) TYPE: Amino Acid
        (D) TOPOLOGY: Linear (xi) SEQUENCE DESCRIPTION: SEQ ID NO: 12:

LEU ARG ARG ALA SER LEU GLY
1               5
```

What is claimed:

1. Essentially pure cDNA encoding wild-type GRK5 or GRK6, dominant negative mutations of wild-type GRK5 or GRK6 and fragments thereof for use as probes.

2. Essentially pure cDNA encoding a G protein-coupled receptor kinase having the sequence shown in SEQ ID NO: 1 or SEQ ID NO: 2.

3. A recombinant DNA expression vector containing SEQ ID NO: 1 or SEQ ID NO: 2.

4. A process for preparing an essentially pure G protein-coupled kinase comprising culturing cells hosting an expression vector of claim 3; recovering the G protein-coupled receptor kinase expressed by the cells; and Purifying the G-protein-coupled receptor kinase.

5. The method of claim 4 wherein the selected cells are Sf9 insect cells.

6. A cell line comprising Sf9 insect cells capable of expressing a G protein-coupled receptor kinase comprising wild-type GRK5 or GRK6, dominant negative mutations of wild-tvye GRK5 or GRK6 and fragments thereof for use as probes.

7. An isolated nucleic acid molecule encoding the amino acid sequence shown in SEQ ID NO: 6.

* * * * *

UNITED STATES PATENT AND TRADEMARK OFFICE
CERTIFICATE OF CORRECTION

PATENT NO.    : 6,255,069 B1
DATED         : July 3, 2001
INVENTOR(S)   : Godowski et al.

It is certified that error appears in the above-identified patent and that said Letters Patent is hereby corrected as shown below:

Column 2,
Line 67, delete "y carboxylated " and insert therefor -- γ carboxylated --.
line 67, to Column 3, line 1 delete "y carboxylated " and insert therefor -- γ carboxylated --.

Column 3,
line 4, delete "y carboxylated "and insert therefor -- γ carboxylated --.

Column 4,
Line 42, delete " protein S." and insert therefor -- protein S --.

Column 6,
Line 25, delete " opendymal " and insert therefor -- ependymal --.

Column 7,
Line 47; delete "a helix " and insert therefor -- α helix --.
Line 49, delete "(.e." and insert therefor -- (i.e. --.

Column 11,
Line 27, delete "V carboxylated " and insert therefor -- γ carboxylated --.
Line 32, delete "y carboxylated " and insert therefor -- γ carboxylated --.
Line 43, delete "polyapitopic" and insert therefor -- polyepitopic --.

Column 15,
Line 64, delete " supre " and insert therefor -- supra --.

Column 18,
Line 29, delete " tee " and insert therefor -- the --.

Column 20,
Lines 4-5, delete " y carboxylated " and insert therefor -- γ carboxylated --.
Line 50, delete " Seccharomyces " and insert therefor -- Sacchapmyces --.

Column 21,
Line 15, delete "nutrtents" and insert therefor -- nutrients --.
Line 53, delete "mathotrexate" and insert therefor -- methotrexate --.
Line 59, delete " endoganous " and insert therefor -- endogenous --.

UNITED STATES PATENT AND TRADEMARK OFFICE
CERTIFICATE OF CORRECTION

PATENT NO.     : 6,255,069 B1
DATED          : July 3, 2001
INVENTOR(S)    : Godowski et al.

It is certified that error appears in the above-identified patent and that said Letters Patent is hereby corrected as shown below:

Column 23,
Line 13, delete " fowipox " and insert therefor -- fowlpox --.
Line 53, delete " Big. " and insert therefor -- Bio. --.
Line 58, delete "Ibp" and insert therefor -- (bp --.

Column 24,
Lines 46-47, delete "V carboxylated" and insert therefor -- γ carboxylated --.

Column 25,
Line 28, delete " *frogills*" and insert therefor -- *fragilis* --.
Line 31, delete "supre" and insert therefor -- supra --.
Line 66, delete " conon " and insert therefor -- cotton --.

Column 26,
Line 44, delete "& L.," and insert therefor -- al., --.
Line 63, delete "potybrene" and insert therefor -- polybrene --.

Column 32,
Line 45, delete " [19941) " and insert therefor -- [1994]) --.
Line 52, delete " DHFFT " and insert therefor -- DHFR⁻ --.

Column 33,
Line 4, delete " in vitr " and insert therefor -- in vitro --.

Column 34,
Line 11, delete " dpi 12.CHO " and insert therefor -- dp12.CH0 --.

Column 35,
Line 9 delete " supematants " and insert therefor -- supernatants --.
Line 27, delete " 1Intergen " and insert therefor -- [Intergen --.

Column 39,
Line 17, delete " Culturina " and insert therefor -- Culturing --.
Line 23, delete " confrim " and insert therefor -- confirm --.

Column 41,
Line 20 delete " sortic " and insert therefor -- aortic --.
Line 34, delete " nomolayer " and insert therefor -- monolayer --.
Line 46, delete " Li 5 " and insert therefor -- L15 --.

UNITED STATES PATENT AND TRADEMARK OFFICE
CERTIFICATE OF CORRECTION

PATENT NO. : 6,255,069 B1
DATED : July 3, 2001
INVENTOR(S) : Godowski et al.

It is certified that error appears in the above-identified patent and that said Letters Patent is hereby corrected as shown below:

Column 61,
Delete "The variant gas6 of claim 2 which is the D domain of gas6." and insert therefor -- Variant gash polypeptide which lacks the A domain of native gas6, wherein said variant polypeptide is the D domain of gas6. --.

Signed and Sealed this

Twenty-fifth Day of June, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO. : 6,255,069 B1
DATED : July 3, 2001
INVENTOR(S) : Jeffrey L. Benovic et al.

It is certified that error appears in the above-identified patent and that said Letters Patent is hereby corrected as shown below:

This certificate supersedes Certificate of Correction issued June 25, 2002, the number was erroneously mentioned and should be deleted since no Certificate of Correction was granted.

Signed and Sealed this

Twenty-fourth Day of September, 2002

Attest:

Attesting Officer

JAMES E. ROGAN
Director of the United States Patent and Trademark Office